US010627408B2

(12) United States Patent
Vojdani

(10) Patent No.: US 10,627,408 B2
(45) Date of Patent: Apr. 21, 2020

(54) METHODS AND APPARATUS FOR DETECTION OF GLUTEN SENSITIVITY, AND ITS DIFFERENTIATION FROM CELIAC DISEASE

(71) Applicant: CYREX LABORATORIES, LLC, Phoenix, AZ (US)

(72) Inventor: Aristo Vojdani, Los Angeles (CA)

(73) Assignee: Cyrex Laboratories, LLC, Phoenix, AZ (US)

( * ) Notice: Subject to any disclaimer, the term of this patent is extended or adjusted under 35 U.S.C. 154(b) by 0 days.

(21) Appl. No.: 15/258,949

(22) Filed: Sep. 7, 2016

(65) Prior Publication Data

US 2016/0377629 A1    Dec. 29, 2016

Related U.S. Application Data

(63) Continuation-in-part of application No. 13/354,119, filed on Jan. 19, 2012, now abandoned.

(51) Int. Cl.
*G01N 33/68* (2006.01)

(52) U.S. Cl.
CPC ... *G01N 33/6854* (2013.01); *G01N 2800/065* (2013.01); *G01N 2800/24* (2013.01)

(58) Field of Classification Search
None
See application file for complete search history.

(56) References Cited

U.S. PATENT DOCUMENTS

| 6,103,480 A * | 8/2000 | Vojdani ............ G01N 33/56916 435/7.2 |
| 6,596,476 B1 * | 7/2003 | Lesniewski .......... C07K 14/005 435/5 |
| 6,703,208 B1 | 3/2004 | Rajadhyaksha et al. |
| 7,462,688 B2 | 12/2008 | Khosla et al. |
| 2003/0109420 A1 * | 6/2003 | Valkirs ................... G01N 33/53 435/7.1 |
| 2006/0286601 A1 * | 12/2006 | Marti .................... C07K 14/415 435/7.1 |
| 2007/0184049 A1 | 8/2007 | Fox |
| 2012/0190571 A1 * | 7/2012 | Vojdani .............. G01N 33/6854 506/9 |

FOREIGN PATENT DOCUMENTS

| EP | 1164375 A1 | 12/2001 |
| EP | 1672368 A1 | 6/2006 |

OTHER PUBLICATIONS

Camarca et al., Intestinal T Cell Responses to Gluten Peptides Are Largely Hetergeneous: Implications for a Peptide-Based Therapy in Celiac Disease, J. Immunol. (2009), 182, p. 4158-4166. (Year: 2009).*
Harlow, E. and Lane, D., Antibodies: A Laboratory Manual (1988) Cold Spring Harbor Laboratory Press, Cold Spring Harbor, NY, pp. 23-26 (Year: 1988).*
Tursi et al., High Prevalence of Celiac Disease Among Patients Affected by Crohn's Disease, Inflamm. Bowel Dis., 11(7), (2005), p. 662-666. (Year: 2005).*
Nelsen et al., Gluten-sensitive enteropathy (Celiac Disease): More Common than you think, American Family Physician, 66(12), (2002), p. 2259-2266 (Year: 2002).*
Brichford, Connie. Celiac Disease and IBS: Differences and Similarities. Everyday Health, 2009. Web. Date Accessed: Oct. 27, 2018. (2 pages) [https://www.everydayhealth.com/celiac-disease/celiac-disease-and-ibs-differences-and-similarities.aspx]. (Year: 2009).*
Vainio et al., Circulating IgA- and IgG-class antigliadin antibodies in dermatitis herpetiformis detected by enzyme-linked immunosorbent assay, Arch Dermatol Res, 275, (1983), pp. 15-18 (Year: 1983).*
Rozenberg, O. et al., "A new algorithm for the diagnosis of celiac disease", Cellular & Molecular Immunology, 2011, vol. 8, pp. 146-149.
Matthias, T. et al., "Diagnostic Challenges in Celiac Disease and the Role of the Tissue Transglutaminase-Neo-Epitope", Clinic Rev Allerg Immunol, 2010, vol. 38, pp. 298-301.
Alessandra Camarca; Intestinal T Cell Responses to Gluten Peptides Are Largely Heterogeneous: Implications for a Peptide-Based Therapy in Celiac Disease; The Journal of Immunology 2009; doi: 10.4049/iimmunol.0803181; 182:4158-4166; 10 pages.
Leszczynska, J. "The use of transglutaminase in the reduction of immunoreactivity of wheat flour," Institiute of General Food Chemistry, Food and Agricultural Immuno9logy, Jan.-Dec. 2006; 17 (1-4): 105-113 Technical University of Lodz, Poland—Jan. 2006 DOI: 10.108/09540100600870279.
Mitea, Cristiana; "Fine specificity of monoclonal antibodies against celiac disease-inducing peptides in the gluteome" American Journal Clinical Nutrition 2008;88:1057-66. Printed in USA. © 2008 American Society for Nutrition.
Fait-Magnusson, K, "Elevated levels of serum antibodies to the lectin wheat germ agglutinin in celiac children lend support to the gluten-lectin theory of celiac disease" Department of Pediatrics, Faculty of Health Sciences, linki:ipIng University, Linkoping, Sweden Copyrixht © Munksgaard 1995.

(Continued)

*Primary Examiner* — Bao Thuy L Nguyen
*Assistant Examiner* — Ellen J Marcsisin
(74) *Attorney, Agent, or Firm* — Fish IP Law, LLP

(57) ABSTRACT

Antibodies are used as biomarkers to assist in distinguishing gluten immune reactivity and sensitivity, silent celiac disease, Crohn's disease and other gut-related pathologies from classical celiac disease. In one class of embodiments, sera, saliva or other samples from a human or other animal are tested for antibodies to (a) a wheat antigen; (b) a gliadin antigen; and (c) one or more of a wheat germ agglutinin, a gluteomorphin, a glutenin, a deamidated glutenin, a prodynorphin, and a dynorphin. Test results are considered particularly interesting where the wheat antigen and the gliadin antigen are both selected from the group consisting of native and deamidated forms of α-gliadin 33-mer, α-gliadin-17-mer, γ-gliadin-15-mer, ω-gliadin-17-mer, and glutenin 21-mer. Test plates and kits can advantageously test for antibodies to at least three, five, seven or all of mixed wheat antigens, α-gliadin, γ-gliadin, ω-gliadin, glutenin, α-glutenin, wheat germ agglutinin, gluteomorphin, prodynorphins, transglutaminase-2, transglutaminase-3, transglutaminase-6, and gliadin-bound transglutaminase.

13 Claims, 5 Drawing Sheets

Specification includes a Sequence Listing.

(56) References Cited

OTHER PUBLICATIONS

D. Agardh et al., "Reduction of tissue transglutaminase autoantibody levels by glutenfree diet is associated with changes in subsets of peripheral blood lymphocytes in children with newly diagnosed coeliac disease" Clinical and Experimental Immunology Original Article doh10.uu./j.1365-2249.2006.03036,x Journal compilation © 2006 British Society for Immunology, Clinical and Experimental Immunology, 144: pp. 67-75.

Aleanzi, M. et al., "Celiac Disease: Antibody Recognition against Native and Selectively Deamidated Gliadin Peptides" Clinical Chemistry 47:11 2023-2028 (2001) © 2001 American Association for Clinical Chemistry 6 pages.

Anderson, LA "Malignancy and mortality in a population-based cohort of patients with coeliac disease or gluten sensitivity" World Journal of Gastroeuterology Jan. 7, 2007; 13(1): 146-151 ISSN I 007-9327 © 2007The WJG Press.

Anderson, R. P. et al. "T cells in peripheral blood after gluten challenge in coeliac disease" Gut 2005 54: pp. 1217-1223 doi: 10.1136/ gut.2004.059998 www.gutjnl.com.

Ankelo, M. "Antibody responses to deamidated gliadin peptide show high specificity and parallel antibodies to tissue transglutaminase in developing coeliac disease" Clinical and Experimental Immunology © 2007 British Society for Immunology, Clinical and Experimental Immunology, 150: pp. 285-293 Original Article doi:to. 1111/i.1365-2249.2007 .03487.x.

Arentz-Hansen, Helene; "The Intestinal T Cell Response to a-Gliadin in Adult Celiac Disease Is Focused on a Single Deamidated Glutamine Targeted by Tissue Transglutaminase" Exp. Med. © The Rockefeller University Press, 0022-1007 /2000/02/603/10 vol. 191. No. 4, Feb. 21, 2000 pp. 603-612; http://www.jem.org.

Arentz-Hansen, Helene; "Celiac Lesion T Cells Recognize Epitopes That Cluster in Regions of Gliadins Rich in Proline Residues," 2002 by the American Gastroenterological Association 0016-5085/02 doi:10.1053/gast.2002.35381; Gastroenterology vol. 123, No. 3.

Baldwin, Michael, "Protein Identification by Mass Spectrometry" Issues in Protein Identification by Mass Spectrometry © 2004 by The American Society for Biochemistry and Molecular Biology, Inc. Molecular & Cellular Proteomics 3.1; 9 pages.

Barnes, R.M.R, et al., "Serum Antibodies Reactive with *Saccharomyces cerevisiae* in Inflammatory Bowel Disease: Is IgA Antibody a Marker for Crohn's Disease?" International Archives of Allergy and Applied Immunology vol. 92, No. 1, 1990. Int Arch Allergy Irrmunol 1990;92:9-15 (DOI: 10.11591000235217).

Barta, Zsolt et al. Seroreactivity against *Saccharom yces cerevisiae* in patients with Crohn's disease and celiac disease World Journal of Gastroenterology Copyright 2003 by The WJG Press ISSN 1007-9327.

Basso, Daniela; Antibodies against Synthetic Deamidated Gliadin Peptides for Celiac Disease Diagnosis and Follow-Up in Children Clinical Chemistry 55:1 pp. 150-157 (2009).

Betterle, Corrado et al. "II. Adrenal Cortex and Steroid 21-Hydroxylase Autoantibodies in Children with Organ-Specific Autoimmune Diseases: Markers of High Progression to Clinical Addison's Disease" 0021-972XI97/S03 00/0, Journal of Clinical Endocrinology and Metabolism Copyright © 1997 The Endocrine Society vol. 82, No. 3.

Betts, M et al., Amino Acid Properties and Consequences of Substitutions Bioinformatics for Geneticists. Chapter 14 Edited by Michael R. Barnes and Ian C. Gray Copyright 2003 John Wiley & Sons, Ltd.ISBNs: 0-470-84393-4 (HB); 0-470-84394-2 (PB) pp. 290-316.

Brown, Amy C. "Gluten sensitivity: problems of an emerging condition separate from celiac disease" Expert Reviews Gastroenterol. Hepatol. 6(1), 43-55 (2012) © 2012 Expert Reviews Ltd ISSN 1747-4124.

Catassi, C. et al., "Celiac Disease" Curr Opin Gastroenterol. 2008;24(6):687-691. © 2008 Lippincott Williams & Wilkins Posted Dec. 5, 2008.

Catassi, C. et al., Detection of Celiac Disease in Primary Care: A Multicenter Case-Finding Study in North America, American Journal of Gastroenterology ISSN 0002-9270 2007 by Am. Coll of Gastroenterology doi: IO. I I I I/i.1572-0241.2007.01173.x Published by Blackwell Publishing.

Chin, Russell L. "Neurologic Complications of Celiac Disease"; Journal of Clinical Neuromuscular Disease vol. 5. No. 3 Mar. 2004, pp. 129-137.

Damoiseaux, J. G.M.C et al., "Diagnostic Value of Anti-*Saccharomyces cerevisiae* and Antineutrophil Cytoplasmic Antibodies for Inflammatory Bowel Disease: High Prevalence in Patients with Celiac Disease" Journal of Clinical Immunology, vol. 22, No. 5, Sep. 2002 (2002).

Dayan, Colin M. et al. "Cronic Autoimmune Thyroiditis" Medical Progress, The New England Journal of Medicine, vol. 335, No. 2; 1996 pp. 99-108.

Dickey, W et al. "Identification of Coeliac Disease in Primary Care" Depts. of Gastroenterology and Histopathology, Altnagelvin Hospital, Londonderry; and Regional Immunology Sen ice, Royal Group of Hospitals, Hclfast Northern Ireland, 3 pages.

Dieterich, W. et al. "Identification of tissue transglutaminase as the autoantigen of celiac disease" © 1997 Nature Medicine, vol. 3, No. 7, Jul. 1997, Nature Publishing Group http://www.nature.com/naturemedicine.

Egan, C.E., "Synergy between intraepithelial lymphocytes and lamina propria T cells drives intestinal inflammation during infection" Nature Publishing Group, vol. 4, No. 6, Nov. 2011. pp. 658-670.

Fleckenstein, B. et al., "Molecular Characterization of Covalent Complexes between Tissue Transglutaminase and Gliadin Peptides" The Journal of Biological Chemistry, vol. 279, No. 17. Issue of Apr. 23, pp. 17607-17616, 2004 © 2004 by The American Society for Biochemistry and Molecular Biology, Inc.

Gao, Y. et al. "Increased Risk for Non-Hodgkin Lymphoma in Individuals With Celiac Disease and a Potential Familial Association" Gastroenterology 2009; vol. 136 No. 1 pp. 91-98 © 2009 by the AGA Institute 0016-5085/09 doi:10.1053/j.gastro.2008.09.031.

Giaffer, M.H. "Antibodies to *Saccharomyces cerevisiae* in patients with Crohn's disease and their possible pathogenic importance," Gut 1992, vol. 33, pp. 1071-1075.

Gurhrie, E. W. et al., "Celiac Disease: More Common Than Once Thought" U.S. Pharmacist Journal 2008;vol. 33 ( 12): pp. 24-29. Copyright © 2000-2012 Jobson Medical Information LLC.

Hadajivassiliou, M. "Headache and CNS white matter abnormalities associated with gluten sensitivity" Neurology 2001; vol. 56:pp. 385-388, Copyright © 2001 by MN Enterprises, Inc.

Harlow, E. et al. Antibodies: A Laboratory Manual, Cold Spring Harbor Laboratory Press 1988, 6 pages.

Iwaniak, A et al. "Biologically Active Peptides Derived From Proteins—A Review" Polish Journal of Food and Nutrition Sciences, 2008. vol. 58. No. 3. pp. 289-29-1.

Jacob, S, et al. "Gluten sensitivity and neuromyelitis optica: two case reports" J Neural Neurosurg Psychiatry 2005; vol. 76: pp. 1028-1030. doi: 10.1136/jnnp.2004.055491.

Johnston, S. "Serological markers for coeliac disease: changes with time and relationship to enteropathy" European Journal of Gastroenterology & Hepatology 1998, vol. 10: pp. 259-264.

Kaser, A. "Inflammatory Bowel Disease" Review in Advance on Jan. 6, 2010 The Annuall Review doi: 10.1146/annurev-imnmnol-030409-101225 Copyright 2010 by Annual Reviews.

Kaukinen, K. et al., "Resurrection of gliadin antibodies in coeliac disease. Deamidated gliadin peptide antibody test provides additional diagnostic benefit" Scandinavian Journal of Gastroenterology, 2007; vol. 42: pp. 1428-1433.

Kitano, N. et al. "Detection of Antibodies against Wheat Germ Agglutinin Bound Glycoproteins on the Islet-cell Membrane" © 1988 by John Wiley & Sons, Ltd. Diabetic Medicine, vol. 5, pp. 139-144 (1988).

Knoflach, P. "Serum antibodies to cow's milk proteins in ulcerative colitis and Crohn's disease" Gastroenterology. Feb. 1987;92 vol. 2, pp. 479-485, (1 page) abstract only.

Kottegen, E. et al. "The Lectin Properties of Gluten as the Basis of the Pathomechanism of Gluten-sensitive Enteropathy" Klin Wochenschr (1983) vol. 61: 111-112.

(56) References Cited

OTHER PUBLICATIONS

Kumar. M. et al. "Atypical Celiac Disease: Could You Be Missing This Common Problem?" Consultant. vol. 50 No. 3 Mar. 3, 2010; 11 pages.

Lanzini, A. "Complete recovery of intestinal mucosa occurs very rarely in adult coeliac patients despite adherence to gluten-free diet" Aliment Phormocol Ther 29, 1299-1308.

Larche, M. et al. Peptide-based therapeutic vaccines for allergic and autoimmune diseases Nature Medicine Supplement vol. 11 No. 4, Apr. 2005 8 Pages.

Leslie, D. et al. "Autoantibodies as predictors of disease" The Journal of Clinical Investigation, Nov. 2001, vol. 108, No. 10, pp. 1417-1422.

Lesie, R.D.G. et al., "Autoantigens IA-2 and GAD in Type I (insulin-dependent) diabetes" Diabetologia © Springer-Verlag 1999 12 pages.

Ludvigsson, J et al., "The Oslo definitions for coeliac disease and related terms" Gut Journal 2012 , 10 pages.

Mace, Gaetane "Anti-μ-opioid-receptor IgG antibodies are commonly present in serum from healthy blood donors: evidence for a role in apoptotic immune cell death" Blood Journal by the American Society of Hematology, Blood, Nov. 1, 2002—vol. 100, No. 9, pp. 3261-3268.

Main, J. et al.,"Antibody to *Saccharomyces cerevisiae* (bakers' yeast) in Crohn's disease" BMJ vol. 297 29 Oct. 11, 1988.

Mamone, G. et al., "Susceptibility to transglutaminase of gliadin peptides predicted by a mass spectrometry-based assay" Federation of European Biochemical Societies( FEBS) Letters 562 (2004) pp. 177-182.

Marsh, M. et al., "Transglutaminase, gluten and celiac disease:Food for thought" pp. 797-801 Nature Medicine—vol. 3—No. 7—Jul. 1997.

Matthias, T. et al., "Novel trends in celiac disease" Cellular & Molecular Immunology (2011) vol. 8, pp. 121-125; published on line Jan. 31, 2011.

Mazzeo, M.F. et al. "Identification of transglutaminase-mediated deamidation sites in a recombinant α-gliadin by advanced mass-spectrometric methodologies" Protein Science (2003), 12:2434-2442. Published by Cold Spring Harbor Laboratory Press. Copyright © 2003 The Protein Society.

McMillan, S. A. et al. "Predictive value for coeliac disease of antibodies to gliadin, endomysium, and jejunum in patients attending for jejuna) biopsy" BMJ British Medical Journal vol. 303, Nov. 9, 1991 3 pages.

Nelsen, D. et al. "Gluten-Sensitive Enteropathy (Celiac Disease): More Common Than You Think" American Family Physician; Dec. 15, 2002 f vol. 66, No. 12; pp. 2259-2266.

Notkins, A. L. "New Predictors of Disease" Scientific Ameircan, Mar. 2007. 9 pages.

Oldfield, W. L. G., W. L. "Allergen-Derived T Cell Peptide-Induced Late Asthmatic Reactions Precede the Induction of Antigen-Specific Hyporesponsiveness in Atopic Allergic Asthmatic Subjects" The Journal of Immunology 2001; 167; 1734-1739.

Quinton, J-F., "Anti-*Saccharomyces cerevisiae* mannan antibodies combined with antineutrophil cytoplasmic autoantibodies in inflammatory bowel disease: prevalence and diagnostic role" Gut 1998; vol. 42:pp. 788-791.

Rubio-Tapia, A. et al., "Increased Prevalence and Mortality in Undiagnosed Celiac Disease" Gastroenterology Jul. 2009; vol. 137: pp. 88-93.

Rumbo, M. "Detection and characterization of antibodies specific to food antigens (gliadin, ovalbumin and β-lactoglobulin) in human serum, saliva, colostrum and milk" Clinical and Experimental Immunology 1998; vol. 122, pp. 453-458.

Sanders, D. S. et al., "Antibody negative coeliac disease presenting in elderly people—an easily missed diagnosis" Clinical review BMJ vol. 330 Apr. 2, 2003, pp. 775-776.

Sapone, A. et al. "Differential Mucosal IL-17 Expression in Two Gliadin-Induced Disorders: Gluten Sensitivity and the Autoimmune Enteropathy Celiac Disease" International Archives of Allergy and Immunology 2010; vol. 152: pp. 75-80.

Sapone, A. et al "Divergence of gut permeability and mucosal immune gene expression in two glutenassociated conditions: celiac disease and gluten sensitivity" BMC Medicine http://www.biomedcentral.com/1741-7015/9/23 11 pages, 2011.

Lu Shan, et al. "Structural Basis for Gluten Intolerance in Celiac Sprue" Science, vol. 297, (2002); Sep. 27, 2002 DOI: 10.1126/science.1074129.

Shor, B-A. D., "Gluten Sensitivity in Multiple Sclerosis Experimental Myth or Clinical Truth?" Contemporary Challenges in Autoimmunity: Annals of the New York Academy of Sciences, vol. 1173: pp. 343-349 (2009). © 2009 New York Academy of Sciences.

Silano, M. et al., 'Bioactive antinutritional peptides derived from cereal prolamins: A Review' Nahrung 43 (1999) Nr. 3, pp. 175-184.

Sjostrom, H. "Identification of a Gliadin T-Cell Epitope in Coeliac Disease: General Importance of Gliadin Deamidation for Intestinal T-Cell Recognition" Scandinavian. Journal of Immunology vol. 48, 111-115, 1998.

Sollid, L. M., "Coeliac Disease: Dissecting a Complex Inflammatory Disorder" Nature Review, vol. 2, Sep. 2002, pp. 647-655.

Sollid, L. M., "Antibodies to wheat germ agglutinin in coeliac disease" Clin. exp. Immunol. (1986) vol. 63, pp. 95-100.

Mowat, A. "Immune responses to dietary antigens: oral tolerance" Immunology Today Apr. 19, 1998, vol. 4: pp. 173-181.

Tanabe, S. "Analysis of Food Allergen Structures and Development of Foods for Allergic Patients" Biosci. Biotechnol. Biochem., 72 (3), pp. 649-659, 2008 Graduate School of Biosphere Science, Hiroshima University, Higashi-hiroshima, Hiroshima 739-8528, Japan Online Publication, Mar. 7, 2008.

Toftedal, P. et al. "Positive predictive value of serological diagnostic measures" in celiac disease Clin Chem Lab Med 2010; 48(5):685-091 DOI 10.1515/CCLM.2010.136.

Tollefsen, S. et al. "HLA-DQ2 and -DQ8 signatures of gluten T cell epitopes in celiac disease" THe Journal of Clinical Investigation, vol. 116, No. 8, Aug. 2006. pp. 2226-2236.

Tursi, A. et al., "High Prevalence of Celiac Disease Among Patients Affected by Crohn's Disease" Inflammatory Bowel Diseases, vol. 11, No. 7, Jul. 2005; pp. 662-666.

Tye-Din, A. J., et al."Comprehensive, Quantitative Mapping of T Cell Epitopes in Gluten in Celiac Disease" Science Translational Medicine 2, 41 ra51 (2010); DOI: 10.1126/scitranslmed.3001012 15 pages.

Vader, W. et al., "The Gluten Response in Children With Celiac Disease Is Directed Toward Multiple Gliadin and Glutenin Peptides" Gastroenterology 2002;122:1729-1737.

Vanderlugt, C. et al., "Epitope Spreading in Immunemediated Diseases: Implications for Immunotherapy" Nature Reviews, vol. 2, Feb. 2002, pp. 86-95.

Wal, Y., "Glutenin is involved in the gluten-driven mucosal T cell response" Eur. Journal of Immunology 1999. 29: pp. 3133-3139.

Verkasal, M. A. et al., "Undiagnosed silent coeliac disease: A risk for underachievement?" Scandinavian Journal of Gastroenterology, 2005; 40: pp. 1407-1412.

Vojdani, A. et al "The Immunology of Immediate and Delayed Hypersensitivity Reaction to Gluten" European Journal of Inflamatory, vol. 6. No. 1, 1-10 (2008).

Vojdani, A. et al "Immune Response to Dietary Proteins, Gliadin and Cerebellar Peptides in Children with Autism" Nutritional Neuroscience, vol. 7, No. 3 (Jun. 2004). pp. 151-161.

Vojdani, A. et al "The Characterization of the Repertoire of Wheat Antigens and Peptides Involved in the Humoral Immune Responses in Patients with Gluten Sensitivity and Crohn's Disease" International Scholarly Research Network vol. 2011, Article ID 950104, 12 pages, doi: I 0.5402/2011/950104.

Vojdani, A. "Antibodies as predictors of autoimmune diseases and cancer" Expert Opinion Immunosciences Lab., Inc., 8693 Wilshire Blvd, Ste. 200, Beverly Hills, CA 90211, USA.

Vojdani, A. "Detection of IgE, IgG, IgA and IgM antibodies against raw and processed food antigens" Published: May 12, 2009I; Nutrition & Metabolism 2009, 6:22 doi: 10.118611743-7075-6-22.

Volta, U. "Celiac disease: diagnostic criteria in progress" Cellular & Molecular Immunology (2011) 8, 96-102 © 2011 CSI and USTC.

(56) References Cited

OTHER PUBLICATIONS

Yang, A. "Inflammatory Bowel Disease in Patients with Celiac Disease" Inflammatory Bowel Disease 2005; vol. 11 : pp. 528-532.
Notification Concerning Transmittal of International Preliminary Report on Patentability (Chapter I of the Patent Cooperation Treaty dated Sep. 26, 2012 issued for PCT/US2012/021892 filed Jan. 19, 2012, (6 pages).

* cited by examiner

FIG. 2

METHODS AND APPARATUS FOR DETECTION OF GLUTEN SENSITIVITY, AND ITS DIFFERENTIATION FROM CELIAC DISEASE

The present application is a continuation in part of U.S. patent application Ser. No. 13/354,119, filed Jan. 19, 2012, which claims the benefit of U.S. Provisional Application No. 61/143,501 filed Jan. 20, 2011, both of which are incorporated herein in their entirety by reference.

FIELD OF THE INVENTION

The present invention relates to methods and kits for aid in diagnosis of gut-related diseases and pathologies, including at least gluten immune reactivity and sensitivity, silent celiac disease, and Crohn's disease.

BACKGROUND

Wheat allergy, celiac disease and gluten sensitivity are three distinct conditions that are triggered by the ingestion of wheat gliadin (1, 2). These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply. In these conditions, the reaction to gluten is mediated by both cellular and humoral immune responses, resulting in the presentation of different symptomatologies. For example, in wheat allergy a specific sequence of gliadin peptides cross-links two IgE molecules on the surface of mast cells and basophils that trigger the release of mediators such as histamines and leukotrienes (3).

Celiac disease (CD) is an autoimmune condition with known genetic makeup and environmental triggers, such as gliadin peptides. CD affects between 1-2% of the general population. Throughout this application, unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Markers for confirming a diagnosis of this disorder are IgA against native, deamidated gliadin peptides and IgA anti-tissue trans glutaminase (tTg) autoantibody. In comparison with 10 CD, gluten sensitivity (GS) affects up to 30% of the population (4). According to two articles published in 2010 and 2011 by Sapone et al (5, 6), symptoms in GS may resemble some of the gastrointestinal symptoms that are associated with CD or wheat allergy, but it is emphasized that objective diagnostic tests for gluten sensitivity are currently missing (5, 6). While studying the innate and immune responses in CD compared to those in GS, the researchers found that TLR1, 15 TLR2 and TLR4, which are associated with innate immunity, were elevated in mucosal GS but not in CD, while biomarkers of adaptive immunity such as IFN-g, IL-21 and IL-17A were expressed in mucosal tissue in CD but not GS. They believed that measurements of toll-like receptors and IFN-y, IL-21 and IL-17A would enable them to differentiate between CD and GS (5, 6) with a method that is highly invasive and would require a biopsy. Immediate type 20 hypersensitivity to gluten is IgE mediated, while delayed type hypersensitivity to gluten is an antibody-(IgG, IgA) and T-cell-mediated reaction, which is called celiac disease or gluten sensitivity with enteropathy (7). In the absence of IgG and IgA against tTg, elevated IgG and IgA against various wheat antigens and peptides indicate the loss of mucosal immune tolerance against wheat peptides and the development of gluten sensitivity (7). Due to antigenic similarities between wheat antigens and human tissue, both CD and GS can result in many autoimmune conditions, including Type 1 diabetes, arthritis, thyroiditis, and even neuroautoimmune conditions such gluten ataxia and multiple sclerosis (8-10).

It should be appreciated that the term "patients" refer to humans under the care of a health care professional. More broadly, however, the novel testing protocols and analyses disclosed herein could be applied to non-patient humans, and any other animal that could suffer from celiac disease, gluten sensitivity, and gut-related autoimmunities.

While GS patients, similar to CD patients, are unable to tolerate gluten and can develop the same or similar sets of gastrointestinal symptoms, in GS this immune reaction does not lead to small intestine damage (5, 6). This lack of induction of intestinal damage in GS and the association of CD with genetic markers HLA DQ2/DQ8 plus small intestinal damage make the diagnosis of CD much easier than GS. The less severe clinical picture in GS, the absence of tTg autoantibodies, and the dismissal of the significance of elevated IgG and IgA autoantibodies against various wheat proteins and peptides by many clinicians makes GS an extremely dangerous disorder. This is because the persistence of IgG and/or IgA antibodies in the blood for long periods of time, along with inducers of inflammatory cascades can result in full-blown autoimmunity. If this were to be the case, due to the severity of the resulting tissue damage even implementation of a gluten-free diet might not be able to help reverse the course of the autoimmune reaction induced by IgG and IgA antibodies against different wheat antigens and peptides.

A comparison between celiac disease and gluten immune reactivity/sensitivity is shown in FIG. 1. According to this model, if two children, one with a negative genetic makeup (HLA DQ2/DQ8−), and the other with positive (HLA DQ2/DQ8+), are exposed to environmental factors, such as Rota virus, bacterial endotoxins, and some medications or their synergistic effects, the result can be a breakdown of mucosal immune tolerance in both children. The induction of mucosal immune tolerance against gliadin results in the production of IgA and/or IgG against native wheat proteins and peptides, which is the next step in the initiation of gluten sensitivity in both individuals that are HLA DQ2/DQ8− and HLA DQ2/DQ8+.

However, in the individual with the positive genetic makeup, the IgG and IgA antibodies against gliadin along with biomarkers of inflammation can activate tTg, induce damage to the villi, and result in villous atrophy. Deamidation of a specific gliadin peptide leads to the formation of a complex between it and the tTg; the presentation of this complex by antigen-presenting cells to T cells and B cells results in IgA or IgG production against tTg, deamidated gliadin and the gliadin-tTg complex. The formation of these antibodies and their detection in blood is the hallmark of CD, which is an inherited condition detected in 1-2% of the population. If CD is left untreated, the outcome could be autoimmunities and cancer.

In comparison, in an individual negative for HLA DQ2/DQ8, this breakdown in immunological tolerance and the concomitant production of IgA and or IgG against native wheat proteins and peptides may activate an inflammatory cascade. In the absence of tTg activation, however, villous atrophy does not occur. Furthermore, gliadin peptides do not go through de-amidation, and consequently IgG and IgA antibodies are produced only against native wheat and gliadin peptides.

With continuous exposure to wheat antigens and continuous mucosal immune tolerance, the wheat antigens and reacting antibodies form an unholy alliance of immune complexes, resulting in severe gluten immune reactivity and sensitivity. This immune reactivity and sensitivity is a non-inherited condition detected in up to 30% of the population. If this disorder is left unchecked, prolonged exposure to IgG and IgA antibodies against wheat antigens and peptides and their cross-reaction with different tissue antigens can result in various autoimmune disorders. Therefore, even in the absence of CD, GS might still provide a productive environment for other gluten-related autoantibodies that attack different organs.

Furthermore, a gluten-free diet usually is only recommended for those who meet the criteria for a diagnosis of CD, not of gluten immune reactivity and sensitivity. Unfortunately, that leaves many gluten-sensitive people suffering unnecessarily with very serious symptoms that put them at risk for complications, conditions that might be resolved with a gluten-free diet, if they only knew.

Thus, a new paradigm is needed for aid in diagnosing and distinguishing among various gut-related diseases, including gluten immune reactivity and sensitivity, silent celiac disease, celiac disease, and gut-related autoimmunity.

SUMMARY OF THE INVENTION

The inventive subject matter of the present invention provides apparatus, systems and methods in which antibodies are used as biomarkers to assist in diagnosing gluten immune reactivity and sensitivity, silent celiac disease, Crohn's disease and other gut-related pathologies. In some embodiments a mixed wheat antigen preparation (for example, a mixture of water-soluble and alcohol-soluble wheat antigens) can be utilized to differentiate wheat sensitivity and/or wheat-related pathologies (for example, through detection of IgG, IgA, IgM, and/or IgE antibodies that bind to a test surface coated with such a mixed wheat antigen preparation) from other pathologies with similar symptoms. In such embodiments further differentiation between specific wheat-related pathologies such as celiac disease, gluten immune reactivity and sensitivity, and gluten immune reactivity and autoimmunity being provided by determination of the presence of IgG, IgA, and/or IgM directed to specific (e.g. single molecular species) antigens.

The test results can advantageously be used to assist in differentiating gluten immune reactivity or sensitivity from celiac disease, especially where the wheat antigen is de-amidated (for example, through the action of transglutaminase at transglutaminase-sensitive sites or synthesis of a corresponding peptide sequence), and the gliadin antigen is selected from the group consisting of an α-gliadin-33-mer (SEQ ID NO. 1, SEQ ID NO. 2), an α-gliadin-17-mer (SEQ ID NO.6, SEQ ID NO. 7), a γ-gliadin-15-mer (SEQ ID NO. 10), an ω-gliadin-17-mer (SEQ ID NO. 13, SEQ ID NO. 14), and glutenin 21-mer (SEQ ID NO.15, SEQ ID NO. 16).

In certain aspects of the present invention, whole blood, blood sera, saliva or other samples from a human or other animal are tested for antibodies to one or more of a γ-gliadin protein or a peptide thereof (such as γ-gliadin-15-mer (SEQ ID NO. 10)), an ω-gliadin protein or a peptide thereof (such as ω-gliadin-17-mer (SEQ ID NO. 14, SEQ ID NO. 15)) wheat germ agglutinin, a gluteomorphin, a glutenin protein or a peptide thereof (such as glutenin-21-mer), a de-amidated glutenin protein or a peptide thereof, a prodynorphin, and a dynorphin.

In certain aspects of the present invention, whole blood, blood sera, saliva or other samples from a human or other animal are tested for antibodies to (a) a wheat antigen; (b) a gliadin antigen; and (c) one or more of a wheat germ agglutinin, a gluteomorphin, a glutenin, a de-amidated glutenin, a prodynorphin, and a dynorphin.

In certain aspects of the present invention, tests are conducted and/or test results are analyzed for antibodies that assist in distinguishing gluten immune reactivity and/or sensitivity, silent or atypical celiac disease relative to patently symptomatic (i.e. classical) celiac disease, Crohn's disease and chronic immune activation. Test plates and kits of particular interest test for antibodies to at least three, five, seven or all of α-gliadin, γ-gliadin, ω-gliadin, glutenin, wheat germ agglutinin, gluteomorphin, prodynorphins, transglutaminase, and gliadin-bound transglutaminase (gliadin-trans glutaminase complex). In certain aspects of the present invention, assays and assay kits of particular interest allow for testing IgA and/or IgG antibodies to one or more wheat antigens, a α-gliadin protein or one or more peptides thereof such as α-gliadin-33-mer (SEQ ID NO. 1, SEQ ID NO. 2) and/or α-gliadin-17-mer (SEQ ID NO. 6, SEQ ID NO. 7), a γ-gliadin protein or one or more peptides thereof such as γ-gliadin-15-mer (SEQ ID NO. 10), an ω-gliadin protein or one or more peptides thereof such as ω-gliadin-17-mer (SEQ ID NO. 13, SEQ ID NO. 14), wheat germ agglutinin, an opioid peptide such as one or more of gluteomorphin, prodynorphin and/or dynorphin, a glutenin protein or one or more peptides thereof such as glutenin-21-mer (SEQ ID NO. 15, SEQ ID NO. 16), de-amidated glutenin protein or one or more peptides thereof, a gliadin-transglutaminase complex or peptide derived therefrom (SEQ ID NO. 19, SEQ ID NO. 20), or combinations thereof.

In certain aspects of the present invention, the detection of antibodies can be performed with an immunoassay, including, but not limited to, ELISA assay, RIA assay, latex agglutination, beads assay, proteomic assays, and other immunoassays known to one of ordinary skill in the art.

Various objects, features, aspects and advantages of the inventive subject matter of the present invention will become more apparent from the following detailed description of preferred embodiments, along with the accompanying drawing figures in which like numerals represent like components.

BRIEF DESCRIPTION OF THE DRAWINGS

Figure 2:
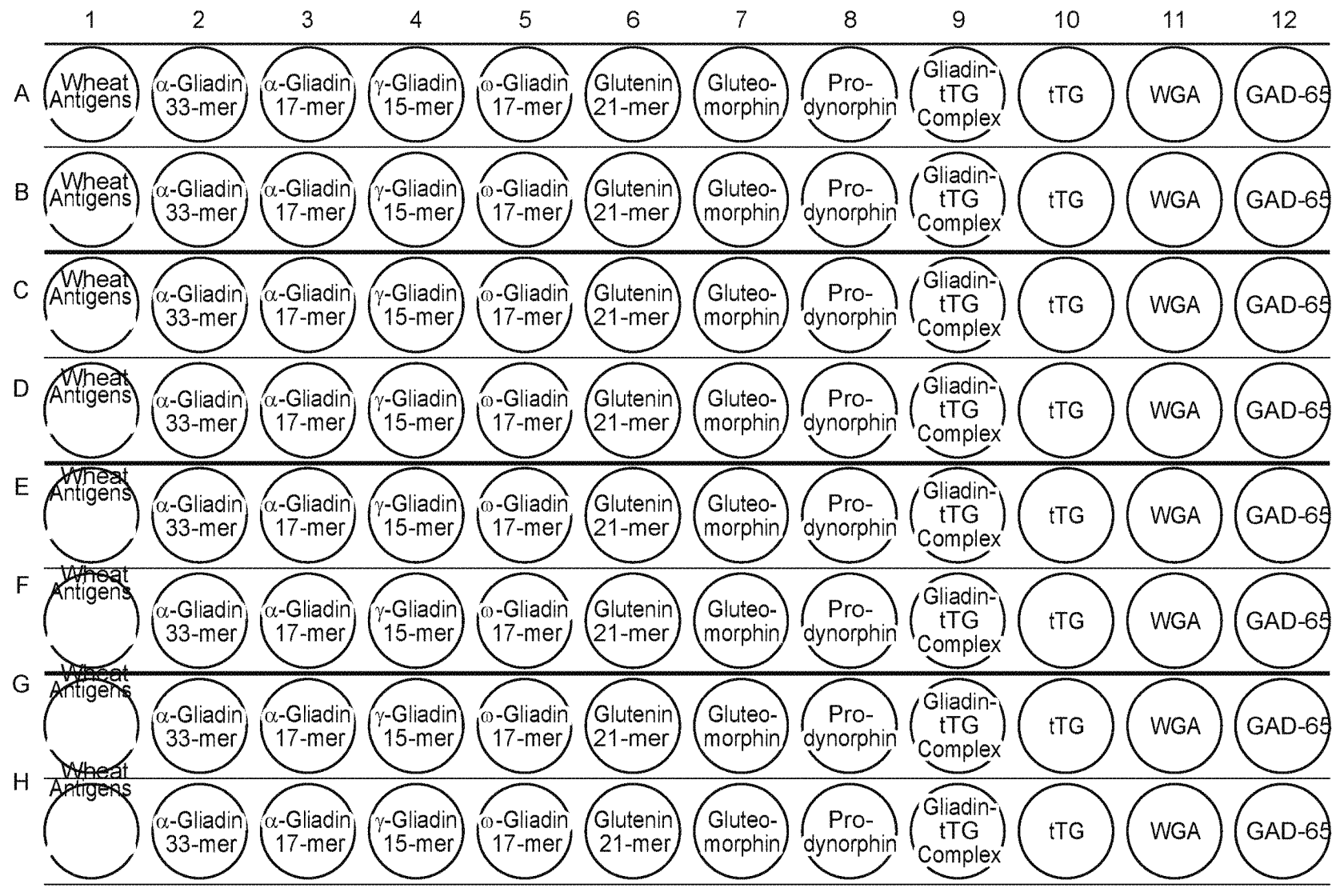

FIG. 2 is a diagram showing the layout of a sample microtiter plate having 12 different rows with 12 different antigens and peptides.

DETAILED DESCRIPTION

Figure 1:
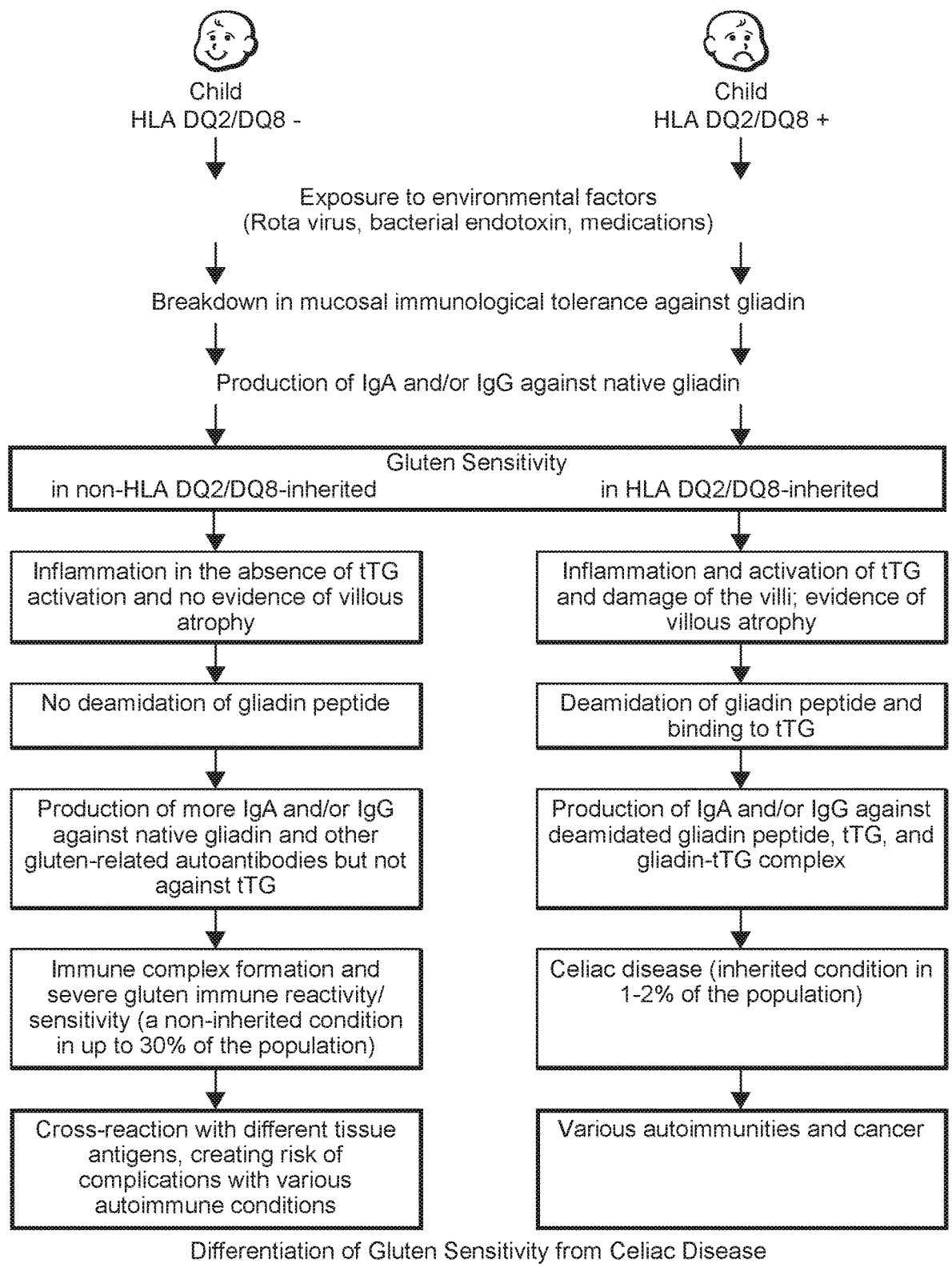
FIG. 1 is a schematic showing differentiation between celiac disease (right hand listing) and gluten immune reactivity/sensitivity (left hand listing), as contemplated herein.

According to certain aspects of the present invention, antibodies are used as biomarkers to assist in diagnosing wheat-related pathologies and distinguishing between gluten immune reactivity and sensitivity, gluten immune reactivity and sensitivity and autoimmunity, silent celiac disease, Crohn's disease, and/or other gut-related pathologies as opposed to the classical celiac disease against an array of wheat antigens and peptides.

In certain aspects of the present invention, a bodily fluid is tested for immunoglobulin G (IgG) and/or immunoglobulin A (IgA) antibodies to one or more of a mixed wheat antigen preparation (i.e. whole-wheat antigen); an α-gliadin protein and/or one or more peptides (at least some of which can be deamidated, for example through the action of a transglutaminase or synthesis of a corresponding peptide sequence) thereof; a γ-gliadin protein and/or one or more peptides (at least some of which can be deamidated, for example through the action of transglutaminase or synthesis of a corresponding peptide sequence) thereof; an ω-gliadin protein and/or one or more peptides (at least some of which can be deamidated, for example through the action of transglutaminase or synthesis of a corresponding peptide sequence) thereof; a glutenin protein and/or one or more peptides (at least some of which can be deamidated, for example through the action of transglutaminase or synthesis of a corresponding peptide sequence) thereof; one or more opioid peptides; a gliadin-trans glutaminase complex (i.e. gliadin complexed transglutaminase or a corresponding peptide); transglutaminase; wheat germ agglutinin; human antigens, and/or combinations thereof.

In certain aspects of the present invention, a mixed wheat antigen preparation (i.e. whole-wheat antigen) can be prepared by combining water-soluble and alcohol-soluble proteins extracted from whole wheat, and in some embodiments some or all of such proteins can be deamidated. The α-gliadin protein and/or one or more peptides thereof can include α-gliadin 33-mer (SEQ ID NO. 1, SEQ ID NO. 2) and/or α-gliadin 17-mer SEQ ID NO.6, SEQ ID NO. 7), with other α-gliadin peptides (for example, α-gliadin 25-mer A (SEQ ID NO. 3), α-gliadin 25-mer B (SEQ ID NO. 4), α-gliadin 18-mer (SEQ ID NO. 5), and/or α-gliadin 15-mer (SEQ ID NO. 8, SEQ ID NO. 9)) contemplated. The γ-gliadin protein and/or one or more peptides thereof includes γ-gliadin-15-mer (SEQ ID NO. 10), with other γ-gliadin peptides (for example, γ-gliadin-20-mer (SEQ ID NO. 11, SEQ ID NO. 12)) contemplated. The ω-gliadin protein and/or one or more peptides thereof includes ω-gliadin 17-mer (SEQ ID NO. 13, SEQ ID NO. 14), with other ω-gliadin peptides contemplated. The glutenin protein or one or more peptides thereof includes glutenin-21-mer (SEQ ID NO. 15, SEQ ID NO. 16), with other glutenin peptides contemplated. It should be appreciated that such gliadin proteins and peptides can, in some embodiments of the inventive concept, be deamidated. Such deamidation can be the result of the action of transglutaminase, which provides deamidation of specific glutamine residues within the protein/peptide sequence, or can be the result of peptide synthesis that replicates the amino acid sequence produced by the action of transglutaminase on a corresponding native peptide sequence. It should be appreciated that the sites of transglutaminase activity are known, and as such the amino acid sequence of such deamidated species is either known or can be readily derived. It should also be appreciated that deamidated peptides can be derived from transglutaminase treatment of native sequences or by synthesis of peptides having sequences corresponding to native sequences having been subjected to transglutaminase activity.

In some embodiments of the inventive concept one or more opioid peptides can be used to determine the presence of antibodies to such peptides, with such characterization providing useful differentiation between wheat-related pathologies. Such one or more opioid peptides includes exorphin peptides including gluteomorphin, prodynorphin and/or dynorphin, with other exorphin peptides contemplated. In some embodiments of the inventive concept one or more human antigens can be used to determine the presence of antibodies to such human antigens, with such characterization providing useful determination between wheat-related pathologies. Such human antigens can be proteins or peptides. Suitable human antigens include glutamic acid decarboxylase (GAD), a cerebellar peptide (i.e. a peptide derived from a cerebellar protein), and other human tissue antigens.

In certain aspects of the present invention, whole blood, blood serum/sera, saliva or other bodily fluid samples from a human or other animal are tested for antibodies to (a) a mixed wheat antigen preparation (i.e. whole wheat antigen); (b) a gliadin antigen; and (c) one or more of a wheat germ agglutinin, gluteomorphin, a glutenin or glutenin peptide (e.g. an α-, γ-, and/or ω-glutenin or glutenin peptide), a de-amidated glutenin or glutenin peptide (e.g. an α-, γ-, and/or ω-glutenin or glutenin peptide deamidated through the activity of transglutaminase or having a corresponding sequence), a prodynorphin, and a dynorphin. Test results are considered particularly interesting where a wheat-derived peptide antigen is deamidated, and the gliadin antigen is selected from the group consisting of α-gliadin 33-mer (SEQ ID NO. 1, SEQ ID NO. 2), α-gliadin 17-mer (SEQ ID NO. 6, SEQ ID NO. 7), α-gliadin 15-mer (SEQ ID NO. 8, SEQ ID NO. 9), ω-gliadin 17-mer (SEQ ID NO. 13, SEQ ID NO. 14), and glutenin-21-mer (SEQ ID NO. 15, SEQ ID NO. 16). Test plates and kits can advantageously test for antigens to at least three, five, seven or all of α-gliadin (and/or peptides thereof), γ-gliadin (and/or peptides thereof), ω-gliadin (and/or peptides thereof), glutenin (and/or peptides thereof), wheat germ agglutinin, gluteomorphin, one or more prodynorphins, transglutaminase, and gliadin-bound transglutaminase (i.e. gliadin-transglutaminase complex). In certain aspects of the present invention, assays and assay kits of particular interest allow for testing IgA and/or IgG antibodies to one or more of mixed wheat antigens, α-gliadin protein or one or more peptides thereof such as α-gliadin-33-mer (SEQ ID NO. 1, SEQ ID NO. 2) and/or α-gliadin-17-mer (SEQ ID NO. 6, SEQ ID NO. 7), γ-gliadin protein or one or more peptides thereof such as γ-gliadin-15-mer (SEQ ID NO. 10), ω-gliadin protein and/or one or more peptides thereof such as ω-gliadin-17-mer (SEQ ID NO. 13, SEQ ID NO. 14), wheat germ agglutinin, an opioid peptide such as one or more of gluteomorphin, prodynorphin and/or dynorphin, glutenin or one or more peptides thereof such as glutenin 21-mer (SEQ ID NO. 15, SEQ ID NO. 16), de-amidated glutenin protein or one or more peptides thereof, gliadin-transglutaminase complex or corresponding peptide (SEQ ID NO. 19, SEQ ID NO. 20), or combinations thereof.

In certain aspects of the present invention, the detection of antibodies can be performed with an immunoassay, including, but not limited to, ELISA assay, RIA assay, latex agglutination, beads assay, proteomic assays, and other immunoassays known to one of ordinary skill in the art.

Following are exemplary descriptions of assays, and their use and analysis with respect to some test patients. Although other materials and methods similar or equivalent to those described herein can be used in the practice or testing of the present invention, the preferred method and materials are now described in the exemplary description of assays to further illustrate the present invention.

Example 1

ELISA Assay

A. Materials And Methods—Plate and Sample Preparation:

Wheat antigens and peptides. A mixed wheat antigen preparation (i.e. whole-wheat antigen) was prepared by combining water-soluble and alcohol-soluble proteins. Different peptides included glutenin 21-mer (SEQ ID NO. 15, SEQ ID NO. 16) and gliadin peptides including α-gliadin 33-mer (SEQ ID NO. 1, SEQ ID NO. 2), α-gliadin 17-mer (SEQ ID NO. 6, SEQ ID NO. 7), γ-gliadin 15-mer (SEQ ID NO. 10), and ω-gliadin 17-mer (SEQ ID NO. 13, SEQ ID NO. 14). In some embodiments deamidated peptides corresponding to one or more of these sequences were produced by synthesizing a peptide sequence corresponding to the sequence of the corresponding native peptide when subjected to transglutaminase activity, where the resulting synthetic peptide reflected a sequence deamidated at transglutaminase-susceptible sites. For example, in some instances a deamidated glutenin 21-mer peptide (SEQ ID NO. 16) was provided by synthesis of a peptide corresponding to that of the corresponding glutenin 21-mer following selective deamidation by transglutaminase. Peptides were synthesized by Bio-Synthesis Inc. (Lewisville, Tex.). Gluteomorphin, prodynorphin, transglutaminases, gliadin-transglutaminase complex (i.e. gliadin bound to transglutaminase), and glutamic acid decarboxylase (GAD-65) were of HPLC grade. Wheat germ agglutinin (WGA) was purchased from Sigma/Aldrich (Saint Louis, Mo.).

The antigens and peptides were dissolved in methanol at a concentration of 1.0 mg/mL, then diluted 1:100 in 0.1 M carbonate-bicarbonate buffer, pH 9.5, and 50 μL were added to each well of a polystyrene flat-bottom ELISA plate. The ELISA plates were incubated overnight at 4° C. and then washed three times with 200 μL Tris-buffered saline (TBS) containing 0.05% Tween 20 (pH 7.4). Non-specific binding of immunoglobulins from samples being characterized was prevented by adding 200 μL of 2% bovine serum albumin (BSA) in TBS to the wells and incubated overnight at 4° C. ELISA plates were washed and after conducting quality control were kept at 4° C. until used.

The enzyme conjugates included: Affinity Purified Antibody Phosphatase-labeled Goat anti-Human IgG (Jackson ImmunoResearch, Cat #109-055-008), and Affinity Purified Phosphatase-labeled Goat anti-Human IgA Antibody (Jackson ImmunoResearch, Cat #109-055-011).

Other additional reagents and materials included in the method as further described herein, include: Phosphate-Buffered Saline Powder (Sigma, Cat # P3813-10PAK), Bovine Serum (Sigma, Cat # P1379-1000ML), Glycerol (Sigma, Cat # GSSI6-S00ML), Sodium Hydroxide (Sigma, Cat # S-5881), Magnesium Chloride (Sigma, Cat #8266), Diethanolamine (Sigma, Cat # D-8885), 1.0 N Hydrochloric Acid Solution (Sigma, Cat # H3162), 5 mg Substrate Tablets: p-NPP (para-nitrophenyl phosphate) (Sigma, Cat # S-0942), and Distilled water (D. H2O).

The microwell plates were prepared and coated with the desired number and types of wheat- and/or human-associated antigens and/or peptides. In the following case examples, 12 different wheat associated antigens and peptides were coated on the microwell plates. Calibrators, positive controls, and diluted patient samples were added to the wells and antibodies recognizing the antigens coated within the test wells were allowed bind during the first incubation. After washing the wells to remove unbound proteins, purified alkaline phosphatase labeled rabbit or goat anti-human IgG and/or anti-human IgA was added to the wells and incubated in a second incubation step. Following the second incubation step unbound alkaline phosphatase labeled antibodies were removed by a further wash step.

Bound alkaline phosphatase (indicating the presence of an IgG:bound antigen or IgA:bound antigen complex within a test well) was visualized by adding paranitrophenyl phosphate (PNPP) substrate, which gives a yellow reaction product, the intensity of which is proportional to the concentration of IgG or IgA antibody specific for the antigen coated within the test well in the sample. Sodium hydroxide was added to each well to stop the reaction. The intensity of color (i.e. optical density) was read at 405 nm.

Plain red top or red "tiger top" tubes (SST tubes) were used for specimen collection, although in certain aspects, other specimen collection apparatus are contemplated for this assay. For example, use of heparin or EDTA plasma is also contemplated. Blood samples were collected using aseptic venipuncture techniques and serum was obtained using standard procedures. In certain aspects it is preferred that a minimum of about 500 μL of serum for the assay, which therefore corresponds to about 0.5 mL or more of blood.

B. Test Assay Procedure

Figure 3:
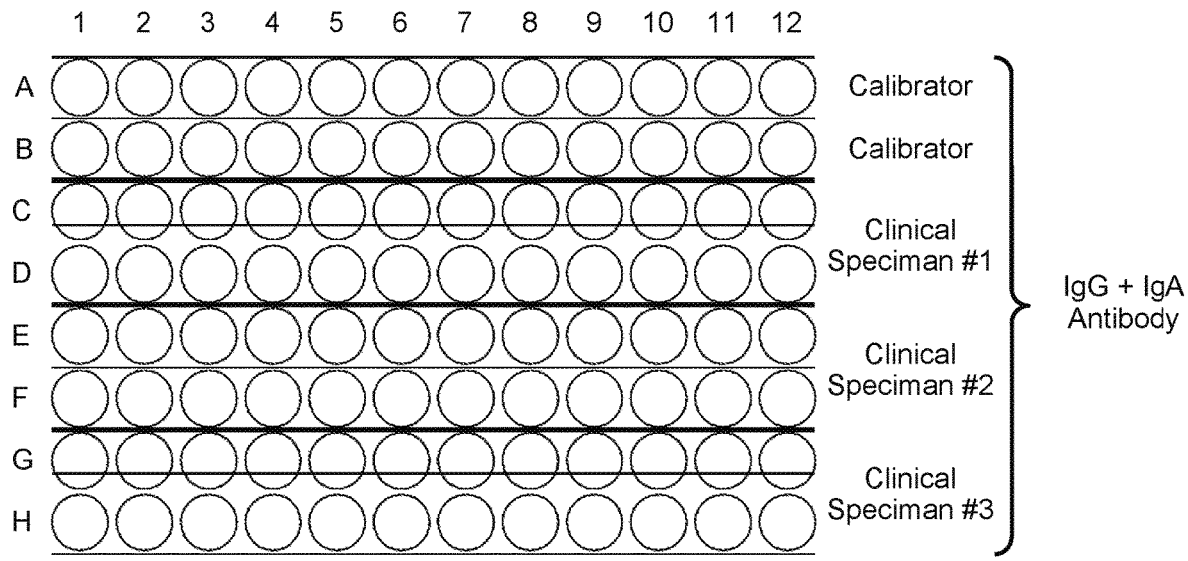
FIG. 3 is a diagram showing the layout of a sample microtiter plate by which IgG or IgA is measured against 12 different antigens or peptides from wheat and associated tissue antigens (antigens or peptides are transparent).
Figure 4:
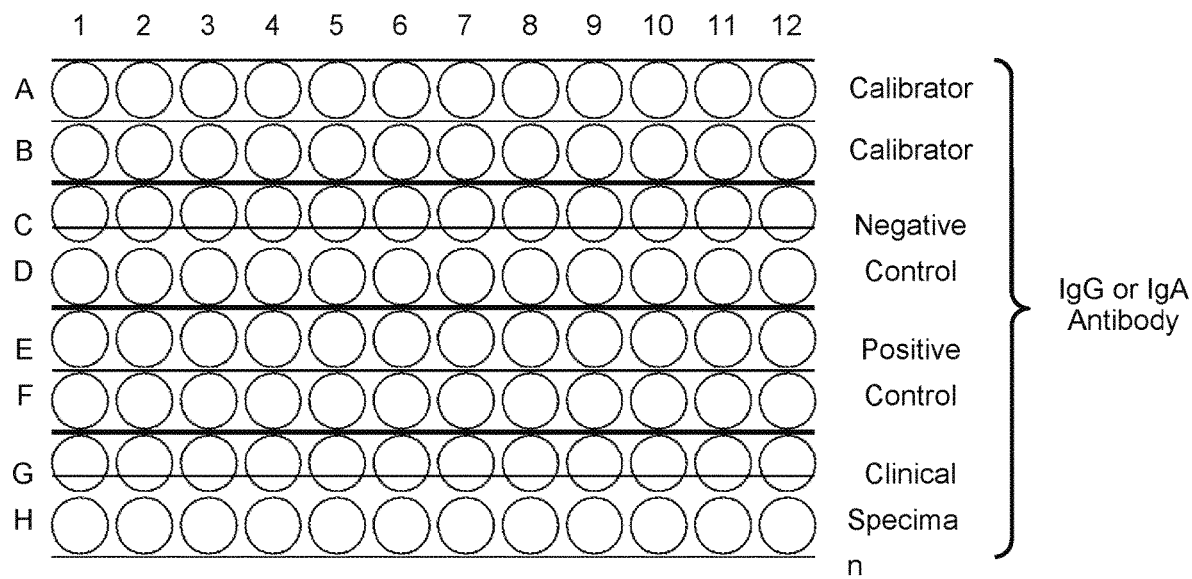
FIG. 4 is a diagram showing the layout of a sample microtiter plate by which IgG or 5 IgA is measured with weekly negative and positive controls for quality control purposes (antigens or peptides are transparent).

The analytical procedure for IgG and/or IgA antibody array to assist in diagnosing and detection of gluten immune reactivity and sensitivity, silent celiac disease, Crohn's disease and other gut-related pathologies is now discussed. In particular, such assays can be used to differentiate wheat-related pathologies from other pathologies having similar symptoms and to differentiate or assist in differentiating between celiac disease, gluten immune reactivity and sensitivity, and gluten immune reactivity and reactivity and autoimmunity. In some aspects, all reagents were allowed to reach room temperature before the test assay was commenced. The test assay procedure includes preparing the desired number of coated wells or plates with the desired number and type of wheat-associated antigens and/or peptides. Once the microtiter wells are prepared, about 100 μL of 1:100 diluted control or calibrator are added to Rows A and B of the microtiter plate as shown in FIG. 3 using a multi-channel pipettor, incubated, and nonspecific binding blocked as described above. About 100 μL of 1:100 diluted patient's test sample, for example blood serum, was added to duplicate wells of rows C and D for Clinical Specimen 1, rows E and F for Clinical Specimen 2, and rows G and H for Clinical Specimen 3. On a separate plate, the periodic negative and positive controls similar to clinical specimens in duplicates were conducted, as shown in FIG. 4. The plates were then incubated for 60 minutes at room temperature. After incubation, the wells were emptied and washed four times with PBS using an ELISA Washer. About 100 µL of optimally diluted alkaline phosphatase-labeled goat anti-human IgA was added to the IgA plate or about 100 µL of enzyme-labeled anti-human IgG was added to the IgG plate at optimal dilution.

The respective plates were then incubated for 30-60 minutes at room temperature. About ten minutes before the conjugate-incubation ended, a substrate solution was prepared by mixing 5 mg of a p-nitrophenyl phosphate tablet with 5 ml of substrate buffer, which was mixed well until the tablet completely dissolved. Following incubation with enzyme labeled anti-human IgA or IgG the plates were washed four times with PBS using an ELISA plate washer. Then, about 100 µL of substrate solution was added to each well. The plate was then incubated for 30 minutes at room temperature with the avoidance of any exposure to direct sunlight. The reaction was stopped by adding about 50 µL of 3 N NaOH. The color intensity (i.e. optical density) of the wells at 405 nm were read using a microtiter plate reader against a blank well, with the absorbance values of the calibrators, controls and unknown samples being recorded.

C. Calculation of Results

After the plate was read the plate at 405 nm to obtain the optical density values (OD405), the mean ODs of the negative controls, the mean ODs of the positive controls and the mean ODs of each clinical specimen were divided by the mean ODs of calibrators on Rows A and B to obtain each Index Value (IV). The Index Value (IV) for each antibody was calculated against the 12 different antigens by dividing the mean OD of each duplicate sample by the mean OD of the calibrator control value (for example, divide the mean OD of wells C1 and D1 by the mean OD of wells A1 and B1, the mean OD of wells C2 and D2 by the mean OD of wells A2 and B2, the mean OD of wells C3 and D3 by the mean OD of wells A3 and B3, etc.). The results were then compared to the established reference ranges. A sample calculation is shown below:

Index Calculation for Wheat Antigens:

Index=(Mean OD of patients)÷(Mean OD of calibrators)

| | |
|---|---|
| Cal 1 (OD) | 0.41 |
| Cal 2 (OD) | 0.44 |
| Sample 3 A (OD) | 3.77 |
| Sample 3 B (OD) | 3.79 |
| Index | 8.93 |

D. Interpretation of Results

Examples of IgG and IgA antibody patterns of 3 patients with celiac disease, 3 patients with gluten immune reactivity and sensitivity, and 3 patients with Crohn's disease with overlapping gluten sensitivity are shown in Tables 2-7. Crohn's disease, also known as regional enteritis, is a type of inflammatory bowel disease having a strong genetic component. It is often described as an autoimmune disease, but others consider it be a disease of immune deficiency.

Data interpretation and laboratory differentiation between celiac disease and gluten immune reactivity/sensitivity/autoimmunity are summarized in Table 8. Peptide sequences for peptides designated in Table 8 and other peptides that are contemplated as useful in such differentiation can be found in Table 9. It should be appreciated that the sequences indicated for gliadin-transglutaminase complex A and gliadin-transglutaminase complex B in Table 9 show the relevant gliadin peptide sequence in parenthesis and imbedded within the relevant transglutaminase peptide sequence, with the relevant gliadin peptide sequence positioned immediately to the right of transglutaminase lysine (K) residue to which it is complexed. In particular, it is now contemplated that celiac disease can be differentiated from silent celiac disease, gluten immune reactivity/sensitivity and/or gluten-related autoimmunity as follows:

a. A serological pattern of silent celiac disease is indicated where the test results include positive results of IgA and/or IgG against any or combination of mixed wheat proteins (i.e. whole wheat antigen), α-gliadin 33-mer (SEQ ID NO. 1), deamidated α-gliadin 33-mer (SEQ ID NO. 2), α-gliadin 25-mer (SEQ ID NO. 3, SEQ ID NO. 4), α-gliadin 18-mer (SEQ ID NO. 5), α-gliadin 17-mer (SEQ ID NO. 6), γ-gliadin15-mer (SEQ ID NO. 10), ω-gliadin 17-mer (SEQ ID NO. 13, SEQ ID NO. 14), glutenin, deamidated glutenin, gluteomorphin, prodynorphin, and wheat germ agglutinin, and negative results against tranglutaminase-2, and at least one of IgA and IgG tests positive against at least one of transglutaminase-3 and transglutaminase-6.

b. A serological pattern of gluten immune reactivity and sensitivity is indicated where the test results include positive results for IgG and/or IgA against mixed wheat proteins (i.e. whole wheat antigen), native α-gliadin, γ-gliadin, ω-gliadin, glutenin, deamidated glutenin, gluteomorphin, and wheat germ agglutinin, but not deamidated α-gliadin and not transglutaminase-2.

c. A diagnosis related to gluten immune reactivity/sensitivity with autoimmunity is indicated where the test results include a positive for IgG and/or IgA against mixed wheat proteins (i.e. whole wheat antigen), native α-gliadin and/or peptides thereof, γ-gliadin and/or peptides thereof, ω-gliadin and/or peptides thereof, glutenin and/or peptides thereof, deamidated glutenin and/or peptides thereof, gluteomorphin, and wheat germ agglutinin, and positive results for any IgG, IgA or IgM to human antigens such as glutamic acid decarboxylase, cerebellar tissue antigens or peptides and/or other human tissue antigens, and negative results for IgA to deamidated α-gliadin, deamidated glutenin or against transglutaminase-2, but positive IgA or IgG against transglutaminase-3 and/or transglutaminase-6.

Reportable ranges and reference ranges are show in Table 1, which may be updated from time to time. The reader will note that compared to established reference ranges at 2 standard deviations above the mean, while IgA antibody against tTg and gliadin-tTg complex is highly positive (confirming the diagnosis of CD), the pattern and the strength of IgG and IgA antibody varies from antigen to antigen. For example, while both IgG and IgA against wheat antigens in all three patients with celiac disease was 4-6 fold higher than reference ranges, when the IgG and IgA was measured against α-gliadin 33-mer the IgG antibody level was significantly elevated in one and the IgA level in two out of three patients (Tables 2 and 3).

When compared to patients with celiac disease, in patients with gluten immune reactivity and sensitivity none of the three patients showed a significant IgA reactivity against tTg and gliadin-tTg complex, while the IgG and IgA antibodies against mixed wheat proteins and in combination with one or more wheat peptides (α-gliadin and/or peptides thereof, γ-gliadin and/or peptides thereof, ω-gliadin and/or peptides thereof, glutenin and/or peptides thereof, gluteomorphin, prodynorphin and wheat germ agglutinin) was significantly elevated. The IgA immune reaction against mixed wheat proteins and wheat derived peptides in combination with tTg and gliadin-tTg complex clearly distinguished between celiac disease and gluten immune reactivity/sensitivity, in which IgG and/or IgA antibodies are reactive against various wheat antigens and peptides but not against tTg and the gliadin-tTg complex (Tables 4, 5).

Tables 6 and 7 present the results of three patients with Crohn's disease. The pattern of IgG and IgA antibodies against tTg and gliadin-tTg complex clearly shows that these patients, in addition to Crohn's disease, are also suffering from gluten immune reactivity/sensitivity, and possibly also celiac disease (Tables 6, 7).

Case Study Examples

Four different case reports, the first on a patient with celiac disease, the second with 10 gluten sensitivity, the third with gluten sensitivity and autoimmunity, and the fourth with gluten sensitivity overlapping with Crohn's disease are shown below.

A. Case Report #1: Diagnosis of Celiac Disease in the Elderly by the Use of IgA against Gliadin and Tissue Transglutaminase with Improvement on a Gluten-Free Diet A 76 year-old man with longstanding dyspepsia, indigestion, tiredness and rapid weight loss was referred for gastrointestinal evaluation. Blood tests showed macrocytic anemia with low concentrations of folate and vitamin B-12. The patient's hemoglobin concentration was 79 g/L, albumin 32 g/L, and transglutaminase 212 µg/mL (normal range=0-10 µg/mL. An urgent colonoscopy and duodenal biopsy was performed, which yielded macrocospically normal results. At this level his IgG and IgA concentrations against gliadin and transglutaminase were checked using FDA-approved kits. Both IgG and IgA against a-gliadin were very high; against transglutaminase, IgA but not IgG was 3.8-fold higher than the reference range. In view of the IgA positivity against gliadin and transglutaminase and diagnosis of celiac disease he was transfused with 2 units of packed cells and started on both a gluten-free diet and 20 mg of prednisone daily. Six months later he had gained about 12 pounds and showed few GI symptoms. Because of this improvement the patient became committed to the gluten-free diet. One year after the first performance of IgG and IgA antibody testing against gliadin and transglutaminase the repeat tests for these antibodies were negative, which is a further indication that disease management plus a gluten-free diet was instrumental in the treatment of this elderly patient with a silent celiac disease.

Discussion: According to Catassi et al. (1, 11), celiac disease (CD) is one of the most common lifelong disorders in western countries. However, most cases of CD remain 10 undiagnosed mostly due to the poor awareness of the primary care physician regarding this important affliction (Catassi C, et al., Am J Gastroenterol, 102:1454-1460,2007). Celiac disease is perceived as presenting GI symptoms accompanied by malabsorption. But many patients with celiac disease do not present GI symptoms. These individuals may have silent or atypical celiac disease, and the condition may present with iron deficiency, anemia, increased liver enzymes, osteoporosis or neurological symptoms (12). As used herein, the term "atypical celiac disease" refers to celiac disease in patients who have only subtle symptoms, and the term "silent celiac disease" refers to celiac disease in patients who are asymptomatic.

The increasing recognition of celiac disease is attributed to the use of new serological assays with higher sensitivity and specificity. Until recently celiac disease was incorrectly 20 perceived as being uncommon and detected mainly during infancy or childhood. However, it is now recognized that most cases of CD occur in adults 40-60 years old. Patients in this age group may present their symptoms, lab test results and other examination signs in atypical fashion. In fact, according to a very recent publication, less than one in seven patients is correctly diagnosed with CD (13). Consequently, as this case shows, if an adult patient presents with symptoms and signs suggesting malabsorption, testing for IgA antibody against gliadin and trans glutaminase should be considered. If the test results are positive, celiac diseases should then be made a part of the differential diagnosis, based on which a gluten-free diet should be recommended. If the gluten-free diet should produce an improvement in symptoms, the patient should commit to the diet regardless of age.

B. Case Report #2: Gluten Immune Reactivity and Sensitivity induced by a Combination of Anesthetics, Antibiotics and Pain Medication A 46 year-old woman was given her yearly checkup by her internist. Based on her medical examination and a normal CBC, chemistry including liver enzymes, and an autoimmune profile, she was classified as a healthy person. Gluten antibodies were not measured at that time. A few months later she went to her dentist for a root canal, bone graft and preparation for dental implantation. During five different visits over ten days she was treated with anesthetic material (mepivacaine), antibiotics and painkillers. Four months later the dental implant procedure was completed after local anesthesia with lidocaine with subsequent prescription of antibiotic (amoxicillin) and painkillers. Four hours later she developed a severe allergic reaction with localized edema, in particular the lips and periorbital area swelling. The patient became agitated and exhibited with a generalized itching, particularly her face, hands and feet. Tightness of the chest with wheezing and difficulty in breathing was an indication of allergic reaction to one or more of the medicines used. She was immediately treated with 0.01 mL per kg of body weight of adrenaline, intramuscularly supplemented by antihistamine treatment. However, while the allergic reaction was controlled, the patient developed severe vomiting and diarrhea with severe abdominal pain, which lasted for 8 days. Two weeks later, while the diarrhea had ameliorated, the patient continued to complain about bloating and abdominal discomfort with irritable bowel like syndrome. She was referred to a GI specialist who detected nothing of note upon a thorough examination. The possibility of gluten sensitivity was then considered, and the patient was tested for HLA typing and IgG and IgA anti-gliadin and anti-transglutaminase antibodies. Immunological tests showed these results: IgG anti-gliadin 6.8 U/mL (normal range <20 U/mL); IgA anti-gliadin 4.1 U/mL (normal range <20 U/mL); IgG anti-tTg 2.1 U/mL (normal range <6 U/mL); IgA anti-tTg 1.2 U/mL (normal range <4 U/mL); and negative for HLA DQ2 and DQ8. Based on these findings gluten sensitivity and celiac disease were excluded, and it was concluded that the patient was suffering from psychogenic or idiosyncratic reaction associated with reaction to the anesthetic and its synergistic effect with the antibiotics. Ninety days later upon her follow-up visit the patient was still complaining about bloating and abdominal pain, particularly 1-3 hours after each meal. Repeat testing was ordered, and both a basic test and a comprehensive test was ordered for anti-gliadin and -tTg IgG and IgA along with ASCA and p¬ANCA IgG, which are the suggested tests for suspected Crohn's disease and ulcerative colitis. Interestingly, almost 100 days after the first GI discomfort, while ASCA and p-ANCA were completely within the normal range, both the IgG and IgA against gliadin were 4 to 9-fold above the reference range (gliadin IgG=79 U/mL; IgA=54 U/mL). However, IgG and IgA antibodies against tTg were within the normal range. In addition, the IgG and IgA antibody testing was performed against an array of wheat, gliadin, glutenin, wheat germ agglutinin, gliadin-tTg complex and tTg antigens. IgG was detected against κ out of 12 tested antigens and IgA against 6 out of 12 tested antigens at 2-7 fold higher than established reference ranges. Both IgG and IgA against tTg and gliadin -tTg complex were negative (see Tables 4 and 5, Sample #1). These results along with the positivity of the basic IgG and IgA test against gliadin but not against transglutaminase showed that the patient, due to allergic reaction to environmental factors, had lost tolerance to wheat antigens and had developed gluten sensitivity but not celiac disease. Despite the absence of elevation in IgG and IgA levels against tTg, due to the continuous GI discomfort and the elevated IgG and IgA against gliadin, a gluten-free diet was recommended, and a dietitian advised the patient to take probiotics and go on a restricted diet free of glutens and also of lectins, since the WGA level was also elevated for both IgG and IgA. Six months after the introduction of the diet and the probiotics, the patient's GI discomfort had subsided and she was back to normal health.

Discussion: The term gluten sensitivity refers to a state of heightened immunological responsiveness to gluten as indicated by the elevation of IgG, IgA or both against gliadin but not against transglutaminase (14). Gluten sensitivity begins with the loss of mucosal immune tolerance to wheat antigens and peptides due to environmental factors affecting the mucosal immune homeostasis.

In this case gluten sensitivity was confirmed based on GI symptoms and immunological testing, in particular IgG and IgA against gliadin and its associated proteins and peptides almost 100 days after the triggering factors had affected her state of immunological tolerance to wheat and associated antigens. It seems that in this patient the synergistic effects of anesthetics, antibiotics and painkillers resulted in dysregulation of her mucosal immune system, followed by a breakdown in immunological tolerance to wheat and other dietary proteins and peptides. This, possibly in combination with the effect of environmental factors on the activity of the digestive enzymes, resulted in the induction of the opening of tight junctions and the entry of undigested wheat proteins and peptides into the submucosa, lymph nodes, and the circulation. These antigens were subsequently presented by antigen-presenting cells to T cells and B cells. During this process gliadin-specific B cells are assisted by gliadin-specific T cells, leading to B-cell clonal expansion and the release of IgG and IgA antibodies to gliadin and associated proteins and peptides, which in this case was detected about 100 days after the original traumatic experience.

It is concluded herein that screening for gluten sensitivity in patients with GI discomfort associated with the use of anesthetics and antibiotics may be easily and cost-effectively undertaken by measuring circulating IgG and IgA against gliadin and associated proteins and peptides. Failure to do so may not only deprive the patient of an accurate diagnosis and the proper treatment by implementation of a gluten-free diet, but may also result in unnecessary medical interventions with their associated side effects.

C. Case Report #3: Gluten Immune Reactivity, Sensitivity and Autoimmunity

Here, a case report is described in which the original presentation led to an erroneous diagnosis of irritable bowel syndrome, resulting in incorrect medical intervention. The correct diagnosis of gluten immune reactivity and sensitivity was made after years of mistreatment.

A 49 year-old woman with abdominal pain, constipation, acid reflux and headache was examined by an internist. Investigation revealed normal CBC with hemoglobin of 10.8 g/dl and normal chemistry profile including liver enzyme. Over several visits detailed biochemical and immunological profiles including ANA, rheumatoid factor, T3, T4, and TSH levels were performed, all testing within the normal range. After repeated complaints about GI discomfort, the patient was referred for GI evaluation. Both endoscopy and *H. pylori* test results were normal. The patient was diagnosed with irritable bowel syndrome and put on ~-blockers and nexium, which moderately improved her symptomatologies. Four years later, however, in addition to the old GI symptoms and headache, she presented symptoms of malaise, blurred vision and facial rash. She was intermittently sleepy and irritable, and experienced breathing problems. Further lab tests revealed her hemoglobin was 9.7 g/dl with MCV of 72 fL, a raised erythrocyte sedimentation rate (46 mm/1st hour), ANA of 1:80 (normal range <40), mild elevation in IgA smooth muscle antibody, double-stranded DNA and extractable nuclear 10 antibodies were negative. Based on the available evidence, a diagnosis of systemic lupus erythematosus (SLE) was made by a rheumatologist, and treatment with steroids was commenced. There was some improvement in her overall state but her hemoglobin level continued to be low, while her ESR fluctuated. Two years later she developed difficulty in passing urine accompanied by tingling and sensory disturbance in her trunk and legs, which led to her being referred to a neurologist. Close questioning revealed a band-like sensation in the trunk and reduced visual acuity (8/46 in the right eye, 8/23 in the left eye) with minimal eye pain, but normal eye movement. Lab investigation came up with low hemoglobin, abnormal MCV, and low serum ferritin at 14 µg/L (normal range 10-150 µg/L), which confirmed iron deficiency. MRI scan of the brain showed extensive white matter abnormalities not typical of multiple sclerosis, but no abnormalities were detected in CSF examination. While blood and CSF examination showed no evidence of bacterial and viral infection including syphilis, mycobacteria, *borrelia*, EBV, CMV, HTLV, and Herpes Type-6, visual evoked potentials showed delay in both optic nerves. In view of these abnormalities, and since tests for gluten sensitivity had not been performed during the earlier investigations, the possibility of gluten sensitivity was considered. A comprehensive IgG and IgA panel was ordered against a repertoire of wheat proteins and peptides, as well as against tTg and various tissue antigens. This comprehensive gluten sensitivity and immune reactivity screen revealed IgG against wheat antigens, α-gliadin 33- and 17-mer, γ- and ω-gliadin, glutenin, gluteomorphin, prodynorphin, gliadin-tTg complex, wheat germ agglutinin, and glutamic acid decarboxylase 65 (GAD-65). IgA antibodies were detected against wheat antigens and wheat germ agglutinin (see Tables 4 and 5, Sample #3). Interestingly, both IgA and IgG tested against tTg were within the normal range. Furthermore, antibodies against ganglioside, cerebellar, synapsin, myelin basic protein, collagen, thyroglobulin and thyroid peroxidase were tested, and all were 2-4 fold above the reference range. Upper GI endoscopy and biopsy revealed normal histology and intraepithelial lymphocytes. Overall the patient was diagnosed as having gluten sensitivity with its associated autoimmunities, including gluten ataxia, headache, white matter abnormalities, and neuromyelitis optica. A five-day course of intravenous methylprednisolone was implemented, and gradually the sensory, motor and visual symptoms improved. In addition, based on the very high levels of IgG and some IgA antibodies against a repertoire of wheat antigens and peptides, a gluten-free diet was introduced, and 12 weeks later marked improvement was observed in the patient's clinical symptomatology. She continued the 100% gluten-free diet under the observation of a dietitian, and the steroid treatment was stopped. Six months after introduction of the diet antibody tests against wheat antigens, peptides, and human tissue were repeated; more than 60% reduction in antibody levels was observed, and the patient became almost asymptomatic. Discussion: From this data it was concluded that a patient may suffer from gluten immune reactivity and sensitivity without having abnormal tissue histology or flat erosive gastritis and antibody against tTg based on which a diagnosis of celiac disease is normally made. If patients with gluten sensitivity and immune reactivity are not detected in time based on the proper lab tests, in particular IgG and IgA antibodies against a repertoire of wheat proteins and peptides, patients' symptomatologies may mislead many clinicians into treating their patients for lupus, MS-like syndrome, neuromyeltitis optica, and many other autoimmune disorders.

Therefore, measurement of IgG and IgA antibodies against a repertoire of wheat antigens and peptides is recommended for patients with signs and symptoms of autoimmunities so that intervention with a gluten-free diet will be instrumental in reversing the autoimmune conditions associated with gluten immune reactivity and sensitivity. Otherwise, untreated and/or mistreated, the patient will develop multiple autoimmune disorders.

D. Case Report #4: Gluten Immune Reactivity and Sensitivity Overlapping with Crohn's Disease Crohn's disease is an inflammatory disorder that often emerges during the second or third 20 decade of life, affecting the terminal ileum in more than two-thirds of patients (15). A combination of genetic and environmental factors, including a shift in gut flora and dysfunctional responses against them, is believed to lead to dysregulated immunity, altered intestinal barrier function, and possibly autoimmunity (16).

Here, a 32 year-old man presented with gastrointestinal discomfort and diarrhea 2-3 times per month. Laboratory results including chemistry panel, CBC, iron, ferritin, transferrin, vitamin B-12, thyroid function, and urine analysis were within the median level of the normal range. Upon the second visit and continuation of GI symptoms he was referred to a GI specialist who ordered additional lab examinations. These tests were microbiological evaluation ofthe stool and blood tests for antibodies against *H. pylori, Saccharomyces* and gliadin. Stool testing with respect to the detection of *Salmonella, Shigella, Yersinia, Campylobacter*, enteropathogenic and enterohemorrhagic *E. coli* or *Clostridium difficile* came out negative. Regarding antibody examinations in the blood, IgG against *H. pylori* and IgA against *Saccharomyces* and gliadin were negative, but IgG against gliadin was moderately elevated at 59 U/mL (normal values=<20 U/mL). The IgG antibody elevations were considered non-specific or protective, and the patient was put on painkillers and sent home with no diagnosis of any specific disorder. Three years later after seeing the frequency ofthe watery diarrhea increase to 3-5 times daily and losing 12 pounds of his body weight in the last two months, the patient went to another GI specialist for a second opinion. Gastric and duodenal biopsies and endoscopy were performed. While the endoscopy of the upper GI tract revealed gastritis of the antrum, histologically, gastric and duodenal biopsy turned out to be negative. D-xylose absorption test was performed; the resulting value of 1.89 g/5 h in urine was suggestive of malabsorption. Immunoserologically ANA titers were below 1:40, p-ANCA and c-ANCA were negative, but the IgA anti-*Saccharomyces* antigen (ASCA) was positive at 85 U/mL (normal=<10 U/mL). Based on the increased frequency of watery diarrhea, abnormal D-xylose absorption, and positive IgA anti-ASCA, the diagnosis of Crohn's disease was made. A therapeutical trial using cholestyramine was initiated but the frequency of the diarrhea remained unchanged. In addition the patient was treated with 230 mg of methylprednisolone, and 2×1000 mg ofmesalazine. Two years after this treatment the patient developed entero-enteric fistulae in the terminal ileum with sigmoid affection. After admission to the hospital, ileocolectomy was performed and 22 cm of the ileum was resected. Upon his release remission maintenance with 3×500 mg ofmesalazine was implemented.

For eight years following this treatment the patient continued to suffer from increasing frequency of watery diarrhea and lost an additional 14 pounds. During this period several additional treatment attempts were made using aspirin, loperamide, and budesonide, unfortunately without significant clinical improvement. Furthermore, the patient was losing more weight on a monthly basis. A complete review of the medical history revealed the fact that almost thirteen years earlier, gliadin IgG antibody had been found to be elevated, which was considered normal at the time. Since all classical treatments for Crohn's disease had failed to improve the clinical picture over all the years, a comprehensive test for the assessment of gluten immune reactivity and sensitivity was ordered. This included IgG and IgA against wheat (i.e. mixed wheat antigens), native and deamidated α-gliadin peptides, γ-gliadin, ω-gliadin, glutenin, gluteomorphin, prodynorphin, gliadin-tTg complex, transglutaminase, wheat germ agglutinin, and GAD-65.

Results depicted in Tables 6 and 7, Sample #3 show that the patient had a significant elevation of IgG antibodies against 11 out of 12 tested antigens, and IgA antibodies against mixed wheat antigens, α-gliadin 33-mer, □-gliadin, prodynorphin, wheat germ agglutinin and GAD-65 were detected at 2-5 fold above the normal range. Based on these results, in addition to Crohn's disease a diagnosis of gluten sensitivity was also made. A diet consisting of rice, potato, and other gluten-free/yeast-free foods was commenced immediately, which led after six weeks to a complete cessation of diarrhea. Upon continuation of the gluten-free diet, not only did stool consistency become normal but the patient also started gaining weight. On follow-up one year later the patient was back to a normal state and had regained more than 80% of his lost weight.

Discussion: This case reports on the association of Crohn's disease with gluten sensitivity but not with celiac disease. Based on the impressive clinical response to the gluten-free diet plus the detection of IgG and IgA antibodies against various wheat antigens, and upon re-evaluation of the IgG antibody level detected 14 years earlier, the diagnosis of Crohn's disease with secondary malabsorption and gluten sensitivity was finally established. Since IgG antibodies against gliadin but not trans glutaminase were detected, it can be argued that in this patient the disease initiated with gluten sensitivity and not Crohn's disease. The initial diagnosis of Crohn's disease was made despite the fact that a demonstration of duration exposure to gluten and risk of autoimmune disorders was published in 1999 (Ventura A et ai., Gastroenterol, 117: 303-310, 1999); unfortunately, this was ignored.

It is contemplated herein that continuous exposure to environmental factors such as wheat 15 antigen induced inflammation for a prolonged period of time, resulting in inflammatory bowel disease or Crohn's disease.

Figure 5:
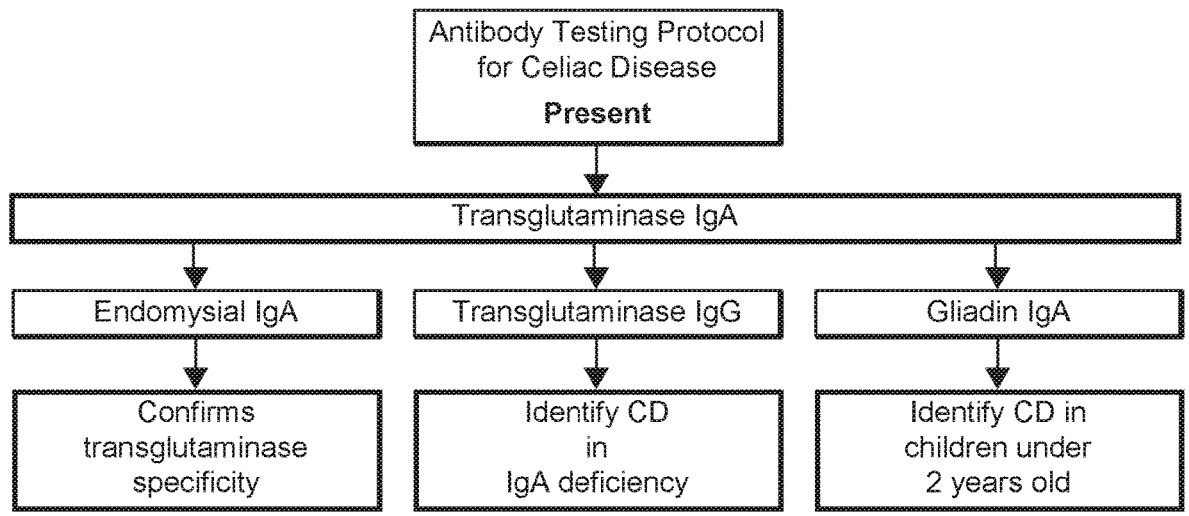
FIG. 5 is a diagram of an antibody testing protocol for celiac disease using tTg and various antigens according to the prior art (17).
Figure 6:
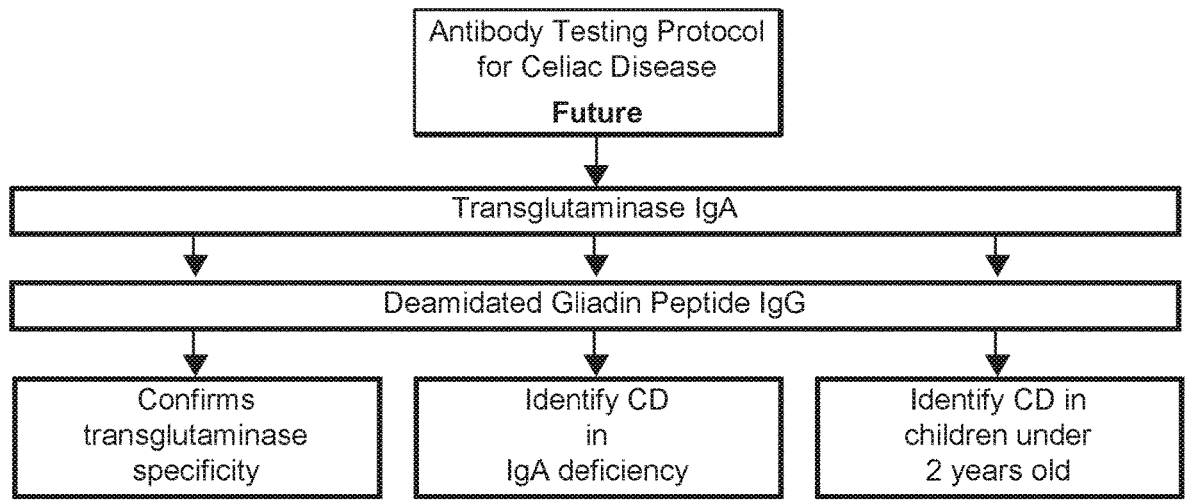
FIG. 6 is a diagram of a testing protocol for celiac disease using deamidated gliadin 10 peptide according to the prior art (17).
Figure 7:
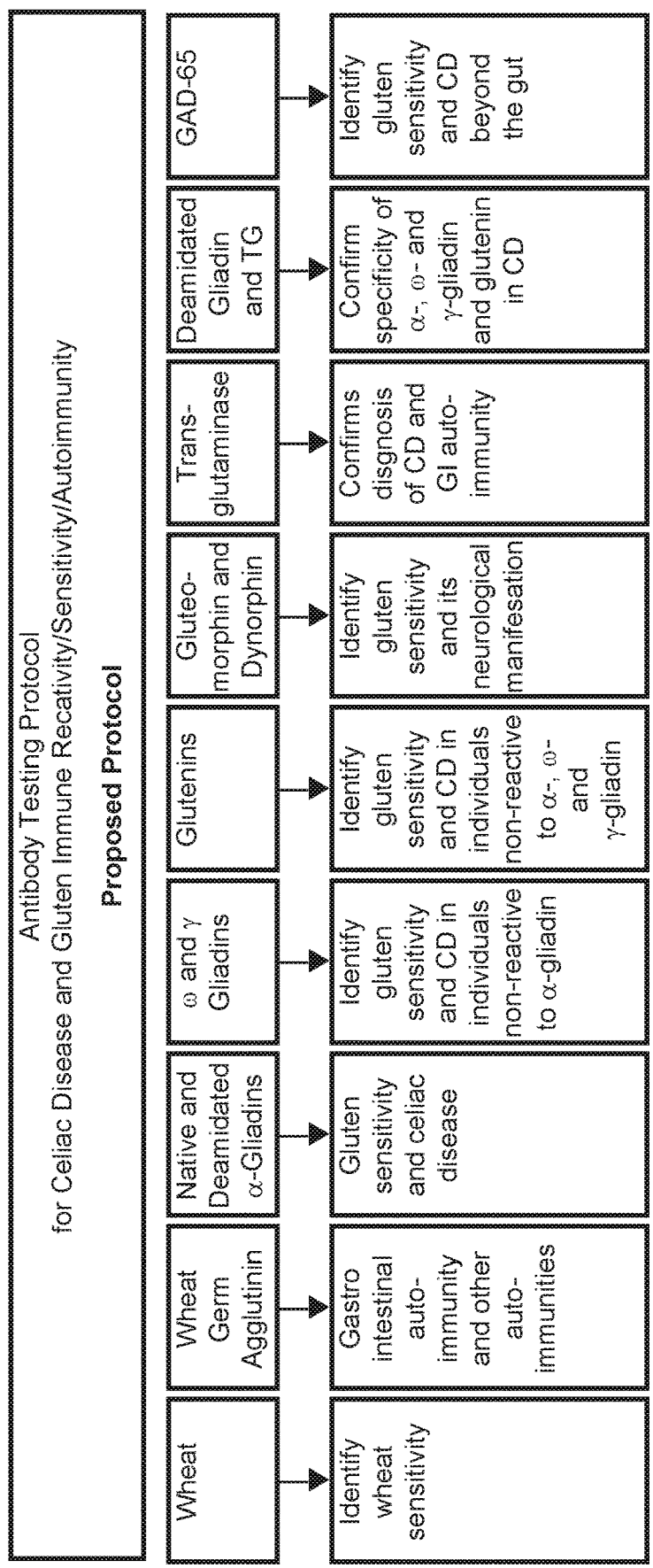
FIG. 7 is a diagram of a testing protocol of the inventive concept for distinguishing wheat-related pathologies from other conditions, and further differentiating between wheat-related pathologies (e.g. celiac disease, gluten immune reactivity and sensitivity, and gluten immune reactivity/sensitivity and autoimmunity) by determining the presence of specific antibodies in a sample using a test antigen repertoire that includes a mixed wheat antigen preparation, wheat antigens and peptides, and other (e.g. human) according to certain aspects of the present invention.

Conclusions Regarding Case Reports: The foregoing case studies show the importance of proper laboratory testing for confirming diagnoses of celiac disease, gluten immune reactivity/sensitivity, and autoimmunity. They show that years of erroneous testing and misdiagnoses can lead to years of suffering. It is vital to get the most accurate information and the most accurate diagnosis, to distinguish between one condition and another. FIGS. 5 and 6 show a summary of the current state of testing as well as a proposed future direction for more accuracy in the diagnosis of celiac disease as proposed by Volta et al. (17). FIG. 7 summarizes an inventive protocol according to certain aspects of the present invention, and proposes testing against a repertoire of wheat antigens and peptides so as to provide the most accurate information and confirmation of celiac disease, Crohn's disease, gluten immune reactivity/sensitivity and autoimmunity.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . . and N, the text should be interpreted as requiring only one element from the group, not A plus N, or B plus N, etc.

REFERENCES

1. Catassi C, Fasano A. Celiac disease. Curr Opin Gastroenterol, 24: 687-691,2008.
2. Anderson L A, McMillan S A, Watson R G, et al. Malignancy and mortality in a population-based cohort of patients with coeliac disease or 'gluten sensitivity.' World J Gastroenterol, 13: 146-151, 2007.
3. Tanabe S. Analysis of food allergen structures and development of foods for allergic patients. Biosci Biotechnol Biochem, 72: 649-659,2008.
4. Chin R L, Latov N, Green P H R, et al. Neurological complications of celiac disease. J Clin Neuromusc Dis, 5: 129-137,2004.
5. Sapone A, Lammers K M, Mazzarella G, et al. Differential mucosal IL-17 expression in two gliadin-induced disorders: gluten sensitivity and the autoimmune enteropathy celiac disease. Int Arch Allergy Immunol. 152: 75-80, 2010.
6. Sapone A, Lammers K M, Casolaro V, et al. Divergence of gut permeability and mucosal immune gene expression in two gluten-associated conditions: celiac disease and gluten sensitivity. BMC Med. 9: 23, 2011.
7. Vojdani A, O'Bryan T, Kellermann G H. The immunology of immediate and delayed hypersensitivity reaction to gluten. Eur. J. Inflamm. 6(1)1-10, 2008.
8. O, Ram M, et al. Gluten sensitivity in multiple sclerosis: experimental myth or clinical truth? Ann N Y Acad Sci, 1173: 343-349, 2009.
9. Vojdani A, O'Bryan T, Green J A, et al. Immune response to dietary proteins, gliadin and cerebellar peptides in children with autism. Nutr Neurasci. 7(3): 151-161, 2004.
10. Hadjivassiliou M, Grunewald R A, Lawden M, et al. Headache and CNS white matter abnormalities associated with gluten sensitivity. Neural, 56: 385-388, 2001.
11. Catassi C, et al. Detection of Celiac disease in primary care: a multicenter case¬20 finding study in North America. Am J Gastroenterol, 102:1454-1460, 2007.
12. Sanders D S, et al. Antibody negative coeliac disease presenting III elderly people—an easily missed diagnosis. BMJ, 330: 775-776, 2005.
13. Matthias T, Neidhofer S, Pfeiffer S, et al. Novel trends in celiac disease. Cell. Mol. Immunol. 8: 121-125, 2011.
14. Jacob S et al. Gluten sensitivity and neuromyelitis optica: Two case reports. J Neural Neurasurg Psychiatry, 76: 1028-1030, 2005.
15. Egan C E, et al. Synergy between intraepithelial lymphocytes and lamina propria T cells drives intestinal inflammation during infection. Mucosal Immunol, 4: 658-670, 2011.
16. Kaser A et al. Inflammatory Bowel Disease. Annu Rev Immunol, 28: 573-621, 2010.
17. Volta U and Villanaci V. Celiac disease: diagnostic criteria in progress. Cell Mol Immunol, 8: 96-102,2011.
18. Vojdani A. 2011. The characterization of the repertoire of wheat antigens and peptides involved in the humoral immune responses in patients with gluten sensitivity and Crohn's disease. ISRN Allergy. Article ID 950104, 1-12.

TABLE 1

Reportable Ranges and Reference Ranges (ELISA Index)

| Antigens | Reportable Range | In Range (Negative) | Equivocal | Out of Range (Positive) | Reference Range |
|---|---|---|---|---|---|
| Wheat IgG | 0.3-6.4 | 0.24-1.0 | 1.01-1.3 | >1.3 | 0.24-1.3 |
| Wheat IgA | 0.4-9.7 | 0.0-1.9 | 1.91-2.4 | >2.4 | 0.0-2.4 |
| α-Gliadin-33 IgG | 0.3-10.0 | 0.16-1.1 | 1.11-1.4 | >1.4 | 0.16-1.4 |
| α-Gliadin-33 IgA | 0.6-16.0 | 0.6-1.5 | 1.51-1.8 | >1.8 | 0.6-1.8 |
| α-Gliadin-17 IgG | 0.3-5.0 | 0.0-1.1 | 1.11-1.5 | >1.5 | 0.0-1.5 |
| α-Gliadin-17 IgA | 0.6-14.8 | 0.4-1.6 | 1.61-2.0 | >2.0 | 0.4-2.0 |
| γ-Gliadin-15 IgG | 0.4-12.0 | 0.14-1.3 | 1.31-1.7 | >1.7 | 0.14-1.7 |
| γ-Gliadin-15 IgA | 0.5-16.0 | 0.7-1.6 | 1.61-1.9 | >1.9 | 0.7-1.9 |
| ω-Gliadin IgG | 0.5-1.0 | 0.24-1.3 | 1.31-1.6 | >1.6 | 0.24-1.6 |
| ω-Gliadin IgA | 0.6-15.4 | 0.6-1.5 | 1.51-1.8 | >1.8 | 0.6-1.8 |
| Glutenin IgG | 0.2-6.0 | 0.0-1.1 | 1.11-1.5 | >1.5 | 0.0-1.5 |
| Glutenin IgA | 0.5-15.9 | 0.5-1.4 | 1.41-1.7 | >1.7 | 0.5-1.7 |
| Gluteomorphin IgG | 0.3-8.0 | 0.12-1.2 | 1.21-1.5 | >1.5 | 0.12-1.5 |
| Gluteomorphin IgA | 0.5-15.1 | 0.6-1.5 | 1.51-1.8 | >1.8 | 0.6-1.8 |
| Prodynorphin IgG | 0.4-13.0 | 0.13-1.7 | 0.131-1.7 | >1.7 | 0.13-1.7 |
| Prodynorphin IgA | 0.6-16.0 | 0.6-1.5 | 1.51-1.8 | >1.8 | 0.6-1.8 |
| Gliadin-tTG Complex IgG | 0.4-13.0 | 0.12-1.2 | 1.21-1.6 | >1.6 | 0.12-1.6 |
| Gliadin-tTG Complex IgA | 0.6-15.5 | 0.5-1.3 | 1.31-1.6 | >1.6 | 0.5-1.6 |
| Transglutaminase IgG | 0.5-12.0 | 0.21-1.1 | 1.11-1.4 | >1.4 | 0.21-1.4 |
| Transglutaminase IgA | 0.5-10.9 | 0.6-1.3 | 0.31-1.5 | >1.5 | 0.6-1.5 |
| Wheat Germ Agglutinin IgG | 0.5-10.0 | 0.17-1.1 | 1.1-1.5 | >1.5 | 0.17-1.5 |
| Wheat Germ Agglutinin IgA | 0.6-16.9 | 0.9-1.6 | 1.61-1.9 | >1.9 | 0.9-1.9 |
| Glutamic Acid Decarboxylase IgG | 0.4-12.0 | 0.29-1.1 | 1.11-1.3 | >1.3 | 0 29-1.3 |
| Glutamic Acid Decarboxylase IgA | 0.8-12.9 | 0.6-1.3 | 1.31-1.5 | >1.5 | 0.6-1.5 |

TABLE 2

IgG Antibody Pattern of 3 Patients with Celiac Disease reacting against various Wheat Antigens,
Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteomorphin | Pro-Dynorphin | Gliadin-tTg Complex | **tTg | Wheat Germ Agglutinin | ***GAD-65 |
|---|---|---|---|---|---|---|---|---|---|---|---|---|
| Cal 1 | 0.41 | 0.33 | 0.35 | 0.32 | 0.51 | 0.40 | 0.50 | 0.38 | 0.39 | 0.46 | 0.37 | 0.38 |
| Cal 2 | 0.44 | 0.35 | 0.35 | 0.32 | 0.25 | 0.43 | 0.49 | 0.37 | 0.40 | 0.44 | 0.36 | 0.42 |
| Sample 1 | 3.77 | 1.04 | 3.86 | 1.02 | 3.84 | 1.34 | 1.44 | 3.84 | 1.76 | 3.83 | 1.15 | 3.81 |
| (OD) | 3.78 | 1.08 | 3.85 | 1.06 | 3.85 | 1.28 | 1.45 | 3.84 | 1.73 | 3.85 | 1.20 | 3.81 |
| Index | 8.91 | 3.11 | 11.02 | 3.26 | 10.14 | 3.19 | 2.92 | 10.32 | 4.43 | 8.55 | 3.24 | 9.52 |
| Sample 2 | 3.85 | 3.87 | 1.13 | 1.10 | 3.86 | 1.08 | 3.84 | 1.26 | 1.37 | 3.84 | 1.45 | 0.98 |
| (OD) | 3.85 | 3.86 | 1.11 | 1.17 | 3.84 | 1.09 | 3.84 | 1.31 | 1.36 | 3.84 | 1.33 | 1.04 |
| Index | 9.09 | 11.32 | 3.21 | 3.55 | 10.15 | 2.63 | 7.76 | 3.44 | 3.46 | 8.55 | 3.83 | 2.53 |
| Sample 3 | 3.77 | 0.89 | 1.11 | 3.53 | 1.23 | 3.37 | 1.31 | 1.15 | 3.84 | 1.37 | 3.84 | 3.54 |
| (OD) | 3.79 | 0.80 | 1.00 | 3.51 | 1.15 | 3.39 | 1.21 | 1.09 | 3.85 | 1.28 | 3.83 | 3.54 |
| Index | 8.93 | 2.46 | 3.03 | 11.05 | 3.14 | 8.23 | 2.55 | 2.99 | 9.74 | 2.95 | 10.56 | 8.85 |

*Native + Deamidated Gliadin 33-mer
**Transglutaminase
***Glutamic Acid Decarboxylase $$\text{Index} = \frac{\text{Mean } OD \text{ of patients}}{\text{Mean } OD \text{ of calibrators}}$$

TABLE 3

IgA Antibody Pattern of 3 Patients with Celiac Disease reacting against various Wheat Antigens,
Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteomorphin | Pro-Dynorphin | Gliadin-tTg Complex | **tTg | Wheat Germ Agglutinin | ***GAD-65 |
|---|---|---|---|---|---|---|---|---|---|---|---|---|
| Cal 1 | 0.36 | 0.37 | 0.36 | 0.36 | 0.31 | 0.41 | 0.43 | 0.39 | 0.39 | 0.37 | 0.41 | 0.48 |
| Cal 2 | 0.39 | 0.37 | 0.36 | 0.36 | 0.39 | 0.41 | 0.43 | 0.41 | 0.39 | 0.38 | 0.39 | 0.39 |
| Sample 1 | 3.00 | 3.64 | 1.23 | 3.82 | 0.47 | 3.82 | 3.83 | 3.39 | 3.83 | 3.84 | 3.87 | 0.83 |
| (OD) | 3.03 | 3.56 | 1.22 | 3.81 | 0.45 | 3.81 | 3.82 | 3.40 | 3.81 | 3.86 | 3.86 | 0.84 |
| Index | 7.97 | 9.69 | 3.43 | 10.67 | 1.31 | 9.42 | 8.88 | 8.51 | 9.84 | 10.29 | 9.69 | 1.93 |
| Sample 2 | 3.55 | 0.96 | 3.83 | 0.95 | 3.82 | 1.75 | 1.31 | 3.82 | 3.87 | 3.85 | 1.65 | 3.80 |
| (OD) | 3.53 | 1.01 | 3.82 | 0.99 | 3.83 | 1.97 | 1.40 | 3.83 | 3.87 | 3.86 | 1.77 | 3.83 |
| Index | 9.34 | 2.65 | 10.69 | 2.71 | 10.96 | 4.59 | 3.14 | 9.60 | 9.98 | 10.30 | 4.28 | 8.83 |
| Sample 3 | 3.81 | 3.84 | 2.99 | 3.83 | 0.99 | 0.40 | 1.85 | 1.33 | 3.83 | 3.85 | 3.81 | 3.48 |
| (OD) | 3.80 | 3.85 | 2.92 | 3.81 | 0.94 | 0.35 | 1.74 | 1.15 | 3.82 | 3.84 | 3.82 | 3.43 |
| Index | 10.05 | 10.36 | 8.27 | 10.68 | 2.76 | 0.92 | 4.16 | 3.11 | 9.86 | 10.26 | 9.56 | 7.99 |

*Native + Deamidated Gliadin 33-mer
**Transglutaminase
***Glutamic Acid Decarboxylase $$\text{Index} = \frac{\text{Mean } OD \text{ of patients}}{\text{Mean } OD \text{ of calibrators}}$$

TABLE 4

IgG Antibody Pattern of 3 Patients with Gluten Immune Reactivity/Sensitivity/Autoimmunity reacting against
various Wheat Antigens, Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteomorphin | Pro-Dynorphin | Gliadin-tTg Complex | **tTg | Wheat Germ Agglutinin | ***GAD-65 |
|---|---|---|---|---|---|---|---|---|---|---|---|---|
| Cal 1 | 0.33 | 0.42 | 0.34 | 0.33 | 0.38 | 0.38 | 0.36 | 0.35 | 0.33 | 0.35 | 0.35 | 0.36 |
| Cal 2 | 0.36 | 0.48 | 0.36 | 0.38 | 0.42 | 0.44 | 0.39 | 0.40 | 0.45 | 0.38 | 0.38 | 0.43 |
| Sample 1 | 3.86 | 0.95 | 3.22 | 1.22 | 0.41 | 1.29 | 1.54 | 3.81 | 0.67 | 0.44 | 1.28 | 1.25 |
| (OD) | 3.87 | 0.88 | 3.26 | 1.26 | 0.33 | 1.34 | 1.36 | 3.84 | 0.64 | 0.41 | 1.31 | 1.20 |
| Index | 11.14 | 2.03 | 9.37 | 3.46 | 0.93 | 3.21 | 3.84 | 10.31 | 1.66 | 1.17 | 3.55 | 3.09 |
| Sample 2 | 3.88 | 3.87 | 2.71 | 2.05 | 3.86 | 1.98 | 1.97 | 1.95 | 0.41 | 0.40 | 1.95 | 2.14 |
| (OD) | 3.88 | 3.87 | 2.65 | 2.10 | 3.85 | 2.28 | 2.20 | 2.19 | 0.37 | 0.41 | 2.18 | 2.21 |
| Index | 11.18 | 8.58 | 7.75 | 5.80 | 9.72 | 5.21 | 5.52 | 5.58 | 1.00 | 1.12 | 5.66 | 5.50 |

TABLE 4-continued

IgG Antibody Pattern of 3 Patients with Gluten Immune Reactivity/Sensitivity/Autoimmunity reacting against various Wheat Antigens, Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteo-morphin | Pro-Dynorphin | Gliadin-tTg Complex | **tTg | Wheat Germ Agglutinin | ***GAD-65 |
|---|---|---|---|---|---|---|---|---|---|---|---|---|
| Sample 3 | 3.85 | 2.44 | 2.38 | 3.86 | 2.41 | 2.50 | 3.86 | 2.49 | 1.49 | 1.00 | 3.86 | 3.88 |
| (OD) | 3.85 | 2.36 | 2.33 | 3.86 | 2.40 | 2.40 | 3.86 | 2.40 | 1.58 | 0.96 | 3.86 | 3.87 |
| Index | 11.10 | 5.33 | 6.81 | 10.79 | 6.05 | 5.99 | 10.23 | 6.60 | 3.91 | 2.69 | 10.59 | 9.79 |

*Native + Deamidated Gliadin 33-mer
**Transglutaminase
***Glutamic Acid Decarboxylase $$\text{Index} = \frac{\text{Mean OD of patients}}{\text{Mean OD of calibrators}}$$

TABLE 5

IgA Antibody Pattern of 3 Patients with Gluten Immune Reactivity/Sensitivity/Autoimmunity reacting against various Wheat Antigens, Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteo-morphin | Pro-Dynorphin | Gliadin-tTg Complex | **tTg | Wheat Germ Agglutinin | ***GAD-65 |
|---|---|---|---|---|---|---|---|---|---|---|---|---|
| Cal 1 | 0.392 | 0.462 | 0.401 | 0.368 | 0.400 | 0.449 | 0.467 | 0.445 | 0.400 | 0.430 | 0.485 | 0.397 |
| Cal 2 | 0.421 | 0.462 | 0.414 | 0.379 | 0.418 | 0.453 | 0.479 | 0.481 | 0.392 | 0.402 | 0.455 | 0.404 |
| Sample 1 | 2.176 | 0.371 | 0.995 | 3.098 | 0.346 | 2.240 | 2.141 | 2.452 | 0.271 | 0.254 | 2.470 | 0.664 |
| (OD) | 2.248 | 0.424 | 0.827 | 3.123 | 0.407 | 2.402 | 2.297 | 2.531 | 0.329 | 0.245 | 2.354 | 0.724 |
| Index | 5.442 | 0.860 | 2.236 | 8.328 | 0.921 | 5.146 | 4.691 | 5.381 | 0.758 | 0.600 | 5.132 | 1.733 |
| Sample 2 | 1.763 | 1.442 | 0.260 | 1.332 | 0.377 | 1.073 | 1.007 | 0.994 | 0.195 | 0.343 | 1.101 | 0.743 |
| (OD) | 1.664 | 1.573 | 0.252 | 1.483 | 0.342 | 1.063 | 1.058 | 1.089 | 0.205 | 0.351 | 1.144 | 0.764 |
| Index | 4.215 | 3.263 | 0.628 | 3.768 | 0.879 | 2.368 | 2.183 | 2.249 | 0.505 | 0.834 | 2.388 | 1.881 |
| Sample 3 | 3.862 | 0.429 | 0.350 | 0.208 | 0.364 | 0.269 | 0.401 | 0.336 | 0.335 | 0.438 | 3.868 | 0.359 |
| (OD) | 3.828 | 0.426 | 0.397 | 0.245 | 0.325 | 0.290 | 0.546 | 0.372 | 0.360 | 0.473 | 3.833 | 0.438 |
| Index | 9.459 | 0.925 | 0.917 | 0.606 | 0.842 | 0.620 | 1.001 | 0.765 | 0.878 | 1.095 | 8.193 | 0.995 |

*Native + Deamidated Gliadin 33-mer
**Transglutaminase
***Glutamic Acid Decarboxylase $$\text{Index} = \frac{\text{Mean OD of patients}}{\text{Mean OD of calibrators}}$$

TABLE 6

IgG Antibody Pattern of 3 Patients with Crohn's Disease reacting against various Wheat Antigens, Peptides and Tissue Antigens expressed as Optical Density with Calculation of Indices

|  | Wheat Antigens | *Alpha Gliadin 33-mer | Alpha Gliadin 17-mer | Gamma Gliadin 15-mer | Omega Gliadin 17-mer | Glutenin 21-mer | Gluteo-morphin | Pro-Dynorphin | Gliadin-tTg Complex | **tTg | Wheat Germ Agglutinin | ***GAD-65 |
|---|---|---|---|---|---|---|---|---|---|---|---|---|
| Cal 1 | 0.45 | 0.41 | 0.38 | 0.39 | 0.36 | 0.39 | 0.55 | 0.47 | 0.71 | 0.49 | 0.41 | 0.55 |
| Cal 2 | 0.38 | 0.33 | 0.44 | 0.44 | 0.37 | 0.40 | 0.54 | 0.56 | 0.60 | 0.49 | 0.48 | 0.46 |
| Sample 1 | 3.74 | 1.56 | 0.65 | 2.29 | 0.56 | 2.10 | 0.54 | 0.69 | 3.81 | 0.81 | 1.23 | 1.83 |
| (OD) | 3.68 | 1.59 | 0.56 | 2.15 | 0.57 | 2.01 | 0.51 | 0.55 | 3.54 | 0.75 | 1.25 | 1.80 |
| Index | 8.97 | 4.26 | 1.47 | 5.30 | 1.54 | 5.22 | 0.96 | 1.19 | 5.59 | 1.59 | 2.79 | 3.59 |
| Sample 2 | 3.87 | 0.47 | 0.72 | 0.55 | 0.59 | 0.49 | 0.52 | 0.44 | 1.04 | 0.76 | 3.83 | 3.87 |
| (OD) | 3.84 | 0.43 | 0.61 | 0.53 | 0.46 | 0.48 | 0.51 | 0.37 | 1.11 | 0.70 | 3.80 | 3.86 |
| Index | 9.31 | 1.22 | 1.62 | 1.29 | 1.43 | 1.23 | 0.94 | 0.78 | 1.63 | 1.49 | 8.62 | 7.63 |
| Sample 3 | 3.86 | 3.79 | 3.86 | 3.67 | 3.85 | 3.24 | 3.84 | 3.86 | 1.71 | 3.80 | 3.82 | 3.84 |
| (OD) | 3.84 | 3.79 | 3.84 | 3.59 | 3.85 | 3.25 | 3.83 | 3.83 | 1.73 | 3.74 | 3.80 | 3.59 |
| Index | 9.31 | 10.23 | 9.33 | 8.67 | 10.51 | 8.22 | 7.03 | 7.43 | 2.62 | 7.71 | 8.60 | 7.34 |

*Native + Deamidated Gliadin 33-mer
**Transglutaminase
***Glutamic Acid Decarboxylase $$\text{Index} = \frac{\text{Mean OD of patients}}{\text{Mean OD of calibrators}}$$

TABLE 7

IgA Antibody Pattern of 3 Patients with Crohn's Disease reacting against various Wheat Antigens Peptides and Tissue Antigens expressed as Optical Density with Calculation of Indices

| Wheat Antigens | *Alpha Gliadin 33-mer | Alpha Gliadin 17-mer | Gamma Gliadin 15-mer | Omega Gliadin 17-mer | Glutenin 21-mer | Gluteo-morphin | Pro-Dynorphin | Gliadin-tTg Complex | **tTg | Wheat Germ Agglutinin | ***GAD-65 |
|---|---|---|---|---|---|---|---|---|---|---|---|
| Cal 1 | 0.37 | 0.39 | 0.40 | 0.39 | 0.43 | 0.43 | 0.46 | 0.47 | 0.41 | 0.42 | 0.48 | 0.42 |
| Cal 2 | 0.45 | 0.44 | 0.46 | 0.42 | 0.47 | 0.51 | 0.54 | 0.50 | 0.48 | 0.48 | 0.49 | 0.47 |
| Sample 1 (OD) | 3.81 | 3.80 | 0.22 | 3.68 | 0.26 | 3.13 | 2.55 | 2.70 | 0.97 | 0.93 | 3.81 | 1.03 |
|  | 3.82 | 3.79 | 0.20 | 3.17 | 0.27 | 3.18 | 2.50 | 2.58 | 1.00 | 0.97 | 3.80 | 1.02 |
| Index | 9.30 | 9.08 | 0.49 | 8.50 | 0.59 | 6.68 | 5.06 | 5.44 | 2.23 | 2.13 | 7.85 | 2.32 |
| Sample 2 (OD) | 3.00 | 0.87 | 0.67 | 0.74 | 0.33 | 0.66 | 1.43 | 1.12 | 0.98 | 0.29 | 1.00 | 1.07 |
|  | 3.43 | 0.85 | 0.64 | 0.70 | 0.32 | 0.66 | 1.12 | 1.03 | 1.00 | 0.31 | 1.02 | 1.10 |
| Index | 7.85 | 2.05 | 1.52 | 1.79 | 0.72 | 1.40 | 2.56 | 2.21 | 2.23 | 0.67 | 2.08 | 2.43 |
| Sample 3 (OD) | 3.89 | 3.56 | 0.99 | 0.99 | 2.25 | 1.05 | 1.12 | 3.85 | 1.00 | 1.18 | 3.73 | 3.87 |
|  | 3.89 | 3.48 | 0.99 | 0.99 | 2.25 | 1.03 | 1.10 | 3.82 | 0.99 | 1.20 | 3.83 | 3.85 |
| Index | 9.48 | 8.43 | 2.27 | 2.45 | 4.98 | 2.20 | 2.23 | 7.90 | 2.25 | 2.65 | 7.79 | 8.69 |

*Native + Deamidated Gliadin 33-mer
**Transglutaminase
***Glutamic Acid Decarboxylase $$\text{Index} = \frac{\text{Mean OD of patients}}{\text{Mean OD of calibrators}}$$

TABLE 8

Sensitivity, and its Differentiation from Celiac Disease

| Antigens and Peptides | Antibody Isotype | Current Testing for Celiac Disease | Proposed Testing for Celiac Disease | Testing Proposed for Celiac Disease in this Patent Application | Testing Proposed for Gluten Immune Reactivity and Sensitivity in this Patent Application | Testing Proposed for Gluten Immune Reactivity, Sensitivity and Autoimmunity in this Patent |
|---|---|---|---|---|---|---|
| α-Gliadin 33-Mer | IgG | + or − | + or − | + or − | + | + |
|  | IgA |  |  |  | + or − | + or − |
| Deamidated α-Gliadin 33-Mer | IgG | + or − | + or − | + or − | − | − |
|  | IgA | + | + | + | − | − |
| Transglutaminase | IgG | + or − | + or − | + or − | + or − | + or − |
|  | IgA | + | + | + | − | − |
| Gliadin Transglutaminase Complex | IgG | Not Tested | + or − | + or − | + or − | + or − |
|  | IgA | Not Tested | + | + | − | − |
| α-Gliadin 17-Mer | IgG | Not Tested | Not Tested | + or − | + | + |
|  | IgA | Not Tested | Not Tested | + | + or − | + or − |
| γ-Gliadin 15-Mer | IgG | Not Tested | Not Tested | + or − | + | + |
|  | IgA | Not Tested | Not Tested | + | + or − | + or − |
| ω-Gliadin 17-Mer | IgG | Not Tested | Not Tested | + or − | + | + |
|  | IgA | Not Tested | Not Tested | + | + or − | + or − |
| Glutenin 21-Mer | IgG | Not Tested | Not Tested | + or − | + | + |
|  | IgA | Not Tested | Not Tested | + | + or − | + or − |
| Deamidated Glutenin 21-Mer | IgG | Not Tested | Not Tested | + or − | − | − |
|  | IgA | Not Tested | Not Tested | + | − | − |
| Gluteomorphin | IgG | Not Tested | Not Tested | + or − | + | + |
|  | IgA | Not Tested | Not Tested | + | + or − | + or − |
| Prodynorphin | IgG | Not Tested | Not Tested | + or − | + | + |
|  | IgA | Not Tested | Not Tested | + | + or − | + or − |
| Wheat Germ Agglutinin | IgG | Not Tested | Not Tested | + or − | + | + |
|  | IgA | Not Tested | Not Tested | + | + or − | + or − |
| Glutamic Acid Decarboxylase | IgG | Not Tested | Not Tested | + or − | + or − | + |
| Cerebellar Peptide | IgG | Not Tested | Not Tested | + or − | + or − | + |
| Other Tissue Antigens | IgG | Not Tested | Not Tested | + or − | + or − | + |

TABLE 9

| Peptide Designation | Amino Acid Sequence | SEQ ID NO. |
|---|---|---|
| α-gliadin 33-iner | LQLQPFPQPQLPYPQPQLPYPQPQLPYPQPQPF | SEQ ID NO. 1 |
| deamidated α-gliadin 33-mer | LQLQPFPQPELPYPQPELPYPQPELPYPQPQPF | SEQ ID NO. 2 |
| α-gliadin 25-mer A | QQQQQQQQQQQKQQQQQQQQILQQ | SEQ ID NO. 3 |
| α-gliadin 25-mer B | QVLQQSTYQLVQQLCCQQLWQIPEQ | SEQ ID NO. 4 |
| α-gliadin 18-mer | QGSVQPQQLPQFEEIRNL | SEQ ID NO. 5 |
| α-gliadin 17-mer | QLQPFPQPQLPYPQPQL | SEQ ID NO 6 |
| deamidated α-gliadin 17-mer | QLQPFPQPELPYPQPEL | SEQ ID NO 7 |
| α-gliadin 15-mer | PFRPQQPYPQPQPQY | SEQ ID NO 8 |
| deamidated α-gliadin 15-mer | PFRPEQPYPQPQPQY | SEQ ID NO. 9 |
| γ-gliadin 15-mer | PQQPQQSFPQQQRPF | SEQ ID NO. 10 |
| γ-gliadin 20-mer | LQPQQPFPQQPQQPYPQQPQ | SEQ ID NO. 11 |
| deamidated γ-gliadin 20-mer | LQPEQPFPEQPQEPYPEQPQ | SEQ ID NO. 12 |
| ω-gliadin 17-mer | QPQQPFPQPQQPFPWQP | SEQ ID NO 13 |
| deamidated ω-gliadin 17-mer | QPEQPFPQPQQPFPWQP | SEQ ID NO. 14 |
| glutenin 21-mer | SHIPGLERPSQQQPLPPQQTL | SEQ ID NO. 15 |
| deamidated glutenin 21-mer | SH1PGLERPSEQQPLPPEQTL | SEQ ID NO. 16 |
| gluteomorphin 35-mer | GYYPTSLQQSGQGQPGYYPTSLQQLGQGQSGYYPTS | SEQ ID NO. 17 |
| prodynorpbin 17-mer | YGGFLRRIRPKLKWDNQ | SEQ ID NO. 18 |
| gliadin-transglutaminase complex A | EDITHTY-K(QLQPFPQPE)-YPEGSSEER | SEQ ID NO. 19 |
| gliadin-transglutaminase complex B | TVEIPDPVEAGEEV-K(PQPQLPYPQPE)-VR | SEQ ID NO. 20 |

---

What is claimed is:

1. A method of producing an antibody profile of an individual, diagnosing and treating a disease in the individual, comprising:
providing, on a microwell plate, (1) a first test surface comprising a first coating comprising a first complex between deamidated a-gliadin 33-mer produced by the action of transglutaminase at transglutaminase-sensitive sites of α-gliadin 33-mer of SEQ ID NO. 1 and a portion of the first test surface, (2) a second test surface comprising a second coating comprising a second complex between transglutaminase-2 and a portion of the second surface, (3) a third test surface comprising a third coating comprising a third complex between deamidated glutenin 21-mer at transglutaminase-sensitive sites of glutenin 21-mer of SEQ ID NO. 15 and a portion of the third test surface, (4) a fourth test surface comprising a fourth coating comprising a fourth complex between a first gliadin antigen and a portion of the fourth test surface, (5) a fifth test surface comprising a fifth coating comprising a fifth complex between a second gliadin antigen and a portion of the fifth surface, and (6) a sixth test surface comprising a sixth coating comprising a sixth complex between a third gliadin antigen and a portion of the sixth test surface;
wherein the first, second and third gliadin antigens are different from each other and are selected from the group consisting of α-gliadin-33-mer of SEQ ID NO. 1, α-gliadin-17-mer of SEQ ID NO. 6, γ-gliadin-15-mer of SEQ ID NO. 10, w-gliadin-17-mer of SEQ ID NO. 13, and glutenin 21-mer of SEQ ID NO. 15;
applying a sample from the individual to the first, second, third, fourth, fifth and sixth test surfaces;
measuring a formation of a complex between IgA immunoglobulins of the sample and the coating of the first test surface, the coating of the second test surface, and the coating of the third test surface;
measuring a formation of a complex between IgG immunoglobulins of the sample and the coating of the fourth test surface, the coating of the fifth test surface, and the coating of the sixth test surface;
obtaining a first, second, third, fourth, fifth and sixth value resulting from measurement of the amount of complex formed between the IgA or IgG immunoglobulins and the coatings of the first, second, third, fourth, fifth, and sixth test surfaces, respectively;
diagnosing the individual with (a) gluten immune reactivity and sensitivity, or (b) gluten immune reactivity and autoimmunity, if the first, second, and third values are negative and the fourth, fifth and sixth values are positive; and
treating the individual diagnosed with (a) or (b) by implementing a gluten free diet.

2. The method of claim 1, wherein the individual is suspected of having Crohn's disease.

3. The method of claim 1, wherein the individual is suspected of having gluten immune reactivity and sensitivity.

4. The method of claim 1, wherein the individual is suspected of having gluten immune reactivity/sensitivity and autoimmunity.

5. The method of claim 1, wherein the individual is suspected of having silent Celiac disease.

6. The method of claim 1, wherein the method provides distinction between a wheat related pathology and a non-wheat related pathology and also provides distinction between a first wheat related pathology and a second wheat related pathology.

7. The method of claim 6, wherein the first wheat related pathology is selected from the list consisting of celiac disease, gluten immune reactivity and sensitivity, and gluten immune reactivity and sensitivity with autoimmunity.

8. The method of claim 7, wherein the second wheat related pathology is selected from the list consisting of celiac disease, gluten immune reactivity and sensitivity, and gluten immune reactivity and sensitivity with autoimmunity.

9. The method of claim 1, wherein the method provides distinction between a wheat related pathology and a non-wheat related pathology and also provides distinction between celiac disease, gluten immune reactivity and sensitivity, and gluten immune reactivity and sensitivity with autoimmunity.

10. The method of claim 1, further comprising:
providing, on the microwell plate, a seventh test surface comprising a seventh coating comprising a seventh complex between a tissue antigen and a portion of the seventh test surface;
applying a sample from the individual to the seventh test surface;
measuring a formation of a complex between IgG immunoglobulins of the sample and the coting of the seventh test surface;
obtaining a seventh value resulting from measurement of the amount of complex formed between the IgG immunoglobulins and the coatings of the seventh test surface; and
diagnosing the individual with gluten immune reactivity and sensitivity, but not gluten immune reactivity and autoimmunity, when the seventh value is negative.

11. The method of claim 10, wherein the tissue antigen is a cerebellar peptide.

12. A method of producing an antibody profile of an individual diagnosing and treating a disease in the individual, comprising:
Providing, on a microwell plate, (1) a first test surface comprising (1) a first test surface comprising a first coating comprising a first complex between deamidated α-gliadin 33-mer produced by the action of transglutaminase at transglutaminase-sensitive sites of α-gliadin 33-mer of SEQ ID NO. 1 and a portion of the first test surface, (2) a second test surface comprising a second coating comprising a second complex between transglutaminase-2 and a portion of the second surface, (3) a third test surface comprising a third coating comprising a third complex between deamidated glutenin 21-mer at transglutaminase-sensitive sites of glutenin 21-mer of SEQ ID NO. 15 and a portion of the third test surface, (4) a fourth test surface comprising a fourth coating comprising a fourth complex between a first gliadin antigen and a portion of the fourth test surface, (5) a fifth test surface comprising a fifth coating comprising a fifth complex between a second gliadin antigen and a portion of the fifth surface, and (6) a sixth test surface comprising a sixth coating comprising a sixth complex between a third gliadin antigen and a portion of the sixth test surface;

wherein the first, second and third gliadin antigens are different from each other and are selected from the group consisting of α-gliadin-33-mer of SEQ ID NO. 1, α-gliadin-17-mer of SEQ ID NO. 6, γ-gliadin-15-mer of SEQ ID NO. 10, w-gliadin-17-mer of SEQ ID NO. 13, and glutenin 21-mer of SEQ ID NO. 15;

applying a sample from the individual to the first, second, third, fourth, fifth, and sixth test surfaces;

measuring a formation of a complex between IgA immunoglobulins of the sample and the coating on the first test surface, the coating on the second test surface, and the coating on the third test surface;

measuring the formation of a complex between IgG immunoglobulins of the sample and the coating of the fourth test surface, the coating of the fifth test surface, and the coating of the sixth test surface;

obtaining a first, second, third, fourth, fifth and sixth value resulting from measurement of the amount of complex formed between the IgA or IgG immunoglobulins and the coatings of the first, second, third, fourth, fifth and sixth test surfaces, respectively;

diagnosing the individual with celiac disease if the first, second, and third values are positive and the fourth, fifth, and sixth values are negative; and treating the individual diagnosed with celiac disease by implementing a gluten free diet.

13. The method of claim 12, wherein implementing a gluten-free diet comprises prescribing a gluten-free diet to the individual.

* * * * *

UNITED STATES PATENT AND TRADEMARK OFFICE
CERTIFICATE OF CORRECTION

PATENT NO. : 10,627,408 B2
APPLICATION NO. : 15/258949
DATED : April 21, 2020
INVENTOR(S) : Aristo Vojdani It is certified that error appears in the above-identified patent and that said Letters Patent is hereby corrected as shown below:

In the Claims

At Column 35, Line 15, change "between deamidated a-gliadin 33-mer" to --between deamidated α-gliadin 33-mer--

At Column 35, Line 39, change "SEQ ID NO. 10, w-gliadin-17-mer" to --SEQ ID NO. 10, ω-gliadin-17-mer--

At Column 36, Line 41, change "the sample and the coting of" to --the sample and the coating of--

At Column 36, Lines 55 and 56, change "Providing, on a microwell plate, (1) a first test surface comprising (1) a first test surface comprising a first" to --providing, on a microwell plate, (1) a first test surface comprising a first--

At Column 37, Line 14, change "of SEQ ID NO. 10, w-gliadin-17-mer" to --of SEQ ID NO. 10, ω-gliadin-17-mer--

Signed and Sealed this
Thirteenth Day of October, 2020

Andrei Iancu
*Director of the United States Patent and Trademark Office*

SEQUENCE LISTING

<160> NUMBER OF SEQ ID NOS: 20

<210> SEQ ID NO 1
<211> LENGTH: 33
<212> TYPE: PRT
<213> ORGANISM: Triticum aestivum
<220> FEATURE:
<221> NAME/KEY: alpha gliadin 33-mer
<222> LOCATION: (1)..(33)

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 2
<211> LENGTH: 33
<212> TYPE: PRT
<213> ORGANISM: Triticum aestivum
<220> FEATURE:

```
<221> NAME/KEY: deamidated alpha gliadin 33-mer
<222> LOCATION: (1)..(33)
<223> OTHER INFORMATION: Sequence represents product of transglutaminase
      activity on native sequence

<400> SEQUENCE: 2

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 3
<211> LENGTH: 25
<212> TYPE: PRT
<213> ORGANISM: Triticum aestivum
<220> FEATURE:
<221> NAME/KEY: alpha gliadin 25-mer A
<222> LOCATION: (1)..(25)

<400> SEQUENCE: 3

Gln Gln Gln Gln Gln Gln Gln Gln Gln Gln Gln Gln Lys Gln Gln Gln
1               5                   10                  15

Gln Gln Gln Gln Gln Ile Leu Gln Gln
            20                  25

<210> SEQ ID NO 4
<211> LENGTH: 25
<212> TYPE: PRT
<213> ORGANISM: Triticum aestivum
<220> FEATURE:
<221> NAME/KEY: alpha gliadin 25-mer B
<222> LOCATION: (1)..(25)

<400> SEQUENCE: 4

Gln Val Leu Gln Gln Ser Thr Tyr Gln Leu Val Gln Gln Leu Cys Cys
1               5                   10                  15

Gln Gln Leu Trp Gln Ile Pro Glu Gln
            20                  25

<210> SEQ ID NO 5
<211> LENGTH: 18
<212> TYPE: PRT
<213> ORGANISM: Triticum aestivum
<220> FEATURE:
<221> NAME/KEY: alpha gliadin 18-mer
<222> LOCATION: (1)..(18)

<400> SEQUENCE: 5

Gln Gly Ser Val Gln Pro Gln Gln Leu Pro Gln Phe Glu Glu Ile Arg
1               5                   10                  15

Asn Leu

<210> SEQ ID NO 6
<211> LENGTH: 17
<212> TYPE: PRT
<213> ORGANISM: Triticum aestivum
<220> FEATURE:
<221> NAME/KEY: alpha gliadin 17-mer
<222> LOCATION: (1)..(17)

<400> SEQUENCE: 6

Gln Leu Gln Pro Phe Pro Gln Pro Glu Leu Pro Tyr Pro Gln Pro Glu
1               5                   10                  15
```

Leu

```
<210> SEQ ID NO 7
<211> LENGTH: 17
<212> TYPE: PRT
<213> ORGANISM: Triticum aestivum
<220> FEATURE:
<221> NAME/KEY: deamidated alpha gliadin 17-mer
<222> LOCATION: (1)..(17)
<223> OTHER INFORMATION: Sequence represents the product of
      transglutaminase activity on the native peptide sequence

<400> SEQUENCE: 7

Gln Leu Gln Pro Phe Pro Gln Pro Glu Leu Pro Tyr Pro Gln Pro Glu
1               5                   10                  15

Leu

<210> SEQ ID NO 8
<211> LENGTH: 15
<212> TYPE: PRT
<213> ORGANISM: Triticum aestivum
<220> FEATURE:
<221> NAME/KEY: alpha gliadin 15-mer
<222> LOCATION: (1)..(15)

<400> SEQUENCE: 8

Pro Phe Arg Pro Gln Gln Pro Tyr Pro Gln Pro Gln Pro Gln Tyr
1               5                   10                  15

<210> SEQ ID NO 9
<211> LENGTH: 15
<212> TYPE: PRT
<213> ORGANISM: Triticum aestivum
<220> FEATURE:
<221> NAME/KEY: deamidated alpha gliadin 15-mer
<222> LOCATION: (1)..(15)
<223> OTHER INFORMATION: Sequence represents product of transglutaminase
      activity with native sequence

<400> SEQUENCE: 9

Pro Phe Arg Pro Glu Gln Pro Tyr Pro Gln Pro Gln Pro Gln Tyr
1               5                   10                  15

<210> SEQ ID NO 10
<211> LENGTH: 15
<212> TYPE: PRT
<213> ORGANISM: Triticum aestivum
<220> FEATURE:
<221> NAME/KEY: gamma gliadin 15-mer
<222> LOCATION: (1)..(15)

<400> SEQUENCE: 10

Pro Gln Gln Pro Gln Gln Ser Phe Pro Gln Gln Gln Arg Pro Phe
1               5                   10                  15

<210> SEQ ID NO 11
<211> LENGTH: 20
<212> TYPE: PRT
<213> ORGANISM: Triticum aestivum
<220> FEATURE:
<221> NAME/KEY: gamma gliadin 20-mer
<222> LOCATION: (1)..(20)

<400> SEQUENCE: 11

Leu Gln Pro Gln Gln Pro Phe Pro Gln Gln Pro Gln Gln Pro Tyr Pro
1               5                   10                  15

Gln Gln Pro Gln
```

```
<210> SEQ ID NO 12
<211> LENGTH: 20
<212> TYPE: PRT
<213> ORGANISM: Triticum aestivum
<220> FEATURE:
<221> NAME/KEY: deamidated gamma gliadin 20-mer
<222> LOCATION: (1)..(20)
<223> OTHER INFORMATION: Sequence represents product of transglutaminase
      activity on native sequence

<400> SEQUENCE: 12

Leu Gln Pro Glu Gln Pro Phe Pro Glu Gln Pro Gln Glu Pro Tyr Pro
1               5                   10                  15

Glu Gln Pro Gln
            20

<210> SEQ ID NO 13
<211> LENGTH: 17
<212> TYPE: PRT
<213> ORGANISM: Triticum aestivum
<220> FEATURE:
<221> NAME/KEY: omega gliadin 17-mer
<222> LOCATION: (1)..(17)

<400> SEQUENCE: 13

Gln Pro Gln Gln Pro Phe Pro Gln Pro Gln Gln Pro Phe Pro Trp Gln
1               5                   10                  15

Pro

<210> SEQ ID NO 14
<211> LENGTH: 17
<212> TYPE: PRT
<213> ORGANISM: Triticum aestivum
<220> FEATURE:
<221> NAME/KEY: deamidated omega gliadin 17-mer
<222> LOCATION: (1)..(17)
<223> OTHER INFORMATION: Sequence represents product of transglutaminase
      activity on native sequence

<400> SEQUENCE: 14

Gln Pro Glu Gln Pro Phe Pro Gln Pro Gln Gln Pro Phe Pro Trp Gln
1               5                   10                  15

Pro

<210> SEQ ID NO 15
<211> LENGTH: 21
<212> TYPE: PRT
<213> ORGANISM: Triticum aestivum
<220> FEATURE:
<221> NAME/KEY: glutenin 21-mer
<222> LOCATION: (1)..(21)

<400> SEQUENCE: 15

Ser His Ile Pro Gly Leu Glu Arg Pro Ser Gln Gln Pro Leu Pro
1               5                   10                  15

Pro Gln Gln Thr Leu
            20

<210> SEQ ID NO 16
<211> LENGTH: 21
<212> TYPE: PRT
<213> ORGANISM: Triticum aestivum
<220> FEATURE:
<221> NAME/KEY: deamidated glutenin 21-mer
```

```
<222> LOCATION: (1)..(21)
<223> OTHER INFORMATION: Sequence represents product of transglutaminase
      activity on native sequence

<400> SEQUENCE: 16

Ser His Ile Pro Gly Leu Glu Arg Pro Ser Glu Gln Gln Pro Leu Pro
1               5                   10                  15

Pro Glu Gln Thr Leu
            20

<210> SEQ ID NO 17
<211> LENGTH: 36
<212> TYPE: PRT
<213> ORGANISM: Triticum aestivum
<220> FEATURE:
<221> NAME/KEY: gluteomorphin 35-mer
<222> LOCATION: (1)..(35)

<400> SEQUENCE: 17

Gly Tyr Tyr Pro Thr Ser Leu Gln Gln Ser Gly Gln Gly Gln Pro Gly
1               5                   10                  15

Tyr Tyr Pro Thr Ser Leu Gln Gln Leu Gly Gln Gly Gln Ser Gly Tyr
            20                  25                  30

Tyr Pro Thr Ser
        35

<210> SEQ ID NO 18
<211> LENGTH: 17
<212> TYPE: PRT
<213> ORGANISM: Homo sapiens
<220> FEATURE:
<221> NAME/KEY: prodynorphin 17-mer
<222> LOCATION: (1)..(17)

<400> SEQUENCE: 18

Tyr Gly Gly Phe Leu Arg Arg Ile Arg Pro Lys Leu Lys Trp Asp Asn
1               5                   10                  15

Gln

<210> SEQ ID NO 19
<211> LENGTH: 17
<212> TYPE: PRT
<213> ORGANISM: Homo sapiens
<220> FEATURE:
<221> NAME/KEY: transglutaminase complex A
<222> LOCATION: (1)..(17)
<223> OTHER INFORMATION: Gliadin complex is formed by coupling of
      gliadin peptide QLQPFPQPE to the lysine at position 8

<400> SEQUENCE: 19

Glu Asp Ile Thr His Thr Tyr Lys Tyr Pro Glu Gly Ser Ser Glu Glu
1               5                   10                  15

Arg

<210> SEQ ID NO 20
<211> LENGTH: 17
<212> TYPE: PRT
<213> ORGANISM: Homo sapiens
<220> FEATURE:
<221> NAME/KEY: transglutaminase complex B
<222> LOCATION: (1)..(17)
<223> OTHER INFORMATION: Gliadin complex is formed by coupling of
      gliadin peptide PQPQLPYPQPE to the lysine at position 15

<400> SEQUENCE: 20
```

-continued

```
Thr Val Glu Ile Pro Asp Pro Val Glu Ala Gly Glu Glu Val Lys Val
1               5                   10                  15
Arg
```